US010452816B2

(12) United States Patent
Kidd et al.

(10) Patent No.: US 10,452,816 B2
(45) Date of Patent: Oct. 22, 2019

(54) METHOD AND SYSTEM FOR PATIENT ENGAGEMENT

(71) Applicant: Catalia Health Inc., San Francisco, CA (US)

(72) Inventors: Cory Kidd, San Francisco, CA (US); Devon Edwards, San Francisco, CA (US); Gary Arnold, San Francisco, CA (US); Brian Mirletz, San Francisco, CA (US); Brien Voorhees, San Francisco, CA (US)

(73) Assignee: Catalia Health Inc., San Francisco, CA (US)

( * ) Notice: Subject to any disclaimer, the term of this patent is extended or adjusted under 35 U.S.C. 154(b) by 0 days.

(21) Appl. No.: 15/428,024

(22) Filed: Feb. 8, 2017

(65) Prior Publication Data
US 2017/0228520 A1    Aug. 10, 2017

Related U.S. Application Data

(60) Provisional application No. 62/292,711, filed on Feb. 8, 2016.

(51) Int. Cl.
*G06F 19/00* (2018.01)
*B25J 11/00* (2006.01)
*G16H 40/63* (2018.01)
*G16H 50/50* (2018.01)

(52) U.S. Cl.
CPC ....... *G06F 19/3481* (2013.01); *B25J 11/0005* (2013.01); *B25J 11/009* (2013.01); *G06F 19/3462* (2013.01); *G16H 40/63* (2018.01); *G16H 50/50* (2018.01)

(58) Field of Classification Search
CPC .............. G06F 19/3481; G06F 19/3418; B25J 11/0005; B25J 11/009; G16H 40/63; G16H 50/50
USPC .......................................................... 705/2
See application file for complete search history.

(56) References Cited

U.S. PATENT DOCUMENTS

| | | | |
|---|---|---|---|
| 7,228,203 B2 | 6/2007 | Koselka et al. |
| 7,337,158 B2 | 2/2008 | Fratkina et al. |
| 7,957,837 B2 | 6/2011 | Ziegler et al. |
| 7,966,093 B2 | 6/2011 | Zhuk |
| 8,684,922 B2 | 4/2014 | Tran |
| 8,935,006 B2 | 1/2015 | Vu et al. |
| 9,286,442 B2 | 3/2016 | Csoma et al. |
| 9,588,519 B2 | 3/2017 | Stubbs et al. |

(Continued)

FOREIGN PATENT DOCUMENTS

WO            042116         3/2013

*Primary Examiner* — Hiep V Nguyen
(74) *Attorney, Agent, or Firm* — Jeffrey Schox

(57) ABSTRACT

Embodiments of a method and system for engaging a patient include receiving a set of user inputs from the patient at an interaction engine associated with a companion robot; at the interaction engine, determining a patient model for the patient; at the interaction engine, determining patient goals for the patient; at the interaction engine, generating an interaction plan including a conversation component and an animation component, based on the patient model and the patient goals; and executing the interaction plan with the companion robot, thereby promoting engagement between the patient and the companion robot, in improving healthcare of the patient.

20 Claims, 13 Drawing Sheets

(56) References Cited

U.S. PATENT DOCUMENTS

| | | |
|---|---|---|
| 2007/0128979 A1 | 6/2007 | Shackelford et al. |
| 2009/0198376 A1* | 8/2009 | Friedman ............... G08C 17/00 |
| | | 700/248 |
| 2012/0303160 A1* | 11/2012 | Ziegler .................... B25J 5/007 |
| | | 700/259 |
| 2014/0277735 A1* | 9/2014 | Breazeal .............. B25J 11/0005 |
| | | 700/259 |
| 2014/0278474 A1 | 9/2014 | McClure et al. |
| 2014/0324216 A1 | 10/2014 | Beg et al. |

* cited by examiner

METHOD AND SYSTEM FOR PATIENT ENGAGEMENT

CROSS-REFERENCE TO RELATED APPLICATIONS

This application claims the benefit of U.S. Provisional Application Ser. No. 62/292,711, filed on 8 Feb. 2016, which is incorporated in its entirety by this reference.

TECHNICAL FIELD

This invention relates generally to the field of healthcare, and more specifically to a new and useful method for patient engagement in the field of healthcare.

BACKGROUND

The number of people for whom health condition monitoring is relevant is significantly rising, and problems associated with this rise include non-adherence to a healthcare regimen. Non-adherence to medication regimens alone costs the U.S. hundreds of billions of dollars each year; however, conventional methods of targeting non-adherence have primarily focused on: intermittent and manual patient check-ins (e.g., in-person check-ins, etc.), education of patients in a non-personalized manner, and analyses of patient adherence at the administrative level. These methods of targeting non-adherence have been largely ineffective at addressing the issue of patient engagement in an effective and personalized manner, as well as promoting adherence to a given regimen, and require additional significant financial and time expenditures. In particular, systems for engaging patients in a manner that accounts for patient personality, patient demographics, and other individual patient features are substantially deficient.

There is thus a need in the field of healthcare to create a new and useful method and system for patient engagement. This invention provides such a new and useful method and system.

DESCRIPTION OF THE EMBODIMENTS

The following description of the preferred embodiment of the invention is not intended to limit the invention to these preferred embodiments, but rather to enable any person skilled in the art to make and use this invention.

1. Overview.

As shown in FIGS. 1A-1C and 2, an embodiment of a method 100 for engaging a patient includes: receiving a set of user inputs from the patient at an interaction engine (e.g., an interaction planning engine) associated with a companion robot Silo; at the interaction engine, determining a patient model (e.g., including a patient-robot relationship model, a personality model, a mood model, a biographical model, a medical model, etc.) for the patient S120; at the interaction engine, determining patient goals (e.g., including patient-robot relationship goals, patient medical goals, etc.) for the patient S125; at the interaction engine, generating an interaction plan including a conversation component and an animation component, based on the patient model and the patient goals S130; and executing the interaction plan with the companion robot, thereby promoting engagement between the patient and the companion robot, in improving healthcare of the patient S140. The method 100 can additionally or alternatively include one or more of: controlling a supplementary device (e.g., a medical device) with the companion robot S150; initiating telecommunication between a patient and a user with the companion robot S160; and/or any other suitable operation.

The method 100 and/or system 200 function to improve treatment management and progression toward health-related goals for a patient, by providing enhanced interactions with a companion robot. As such, one function of the method 100 and/or system 200 is to promote the establishment and maintenance of a strong relationship between the patient and the companion robot. In particular, the method 100 and/or system 200 can receive and process information related to a patient's personality, interests, treatment-related challenges, and goals over time, in order to drive personalized conversations and other interactions with the patient that resonate with the patient's unique personality and circumstances. The method 100 and/or system 200 can additionally or alternatively process data from interactions between the companion robot and the patient and/or interactions between additional companion robots and additional patients, in order to further refine models that guide outputs of one or more companion robots, in improving future interactions between the companion robots and the patients.

Figure 10:
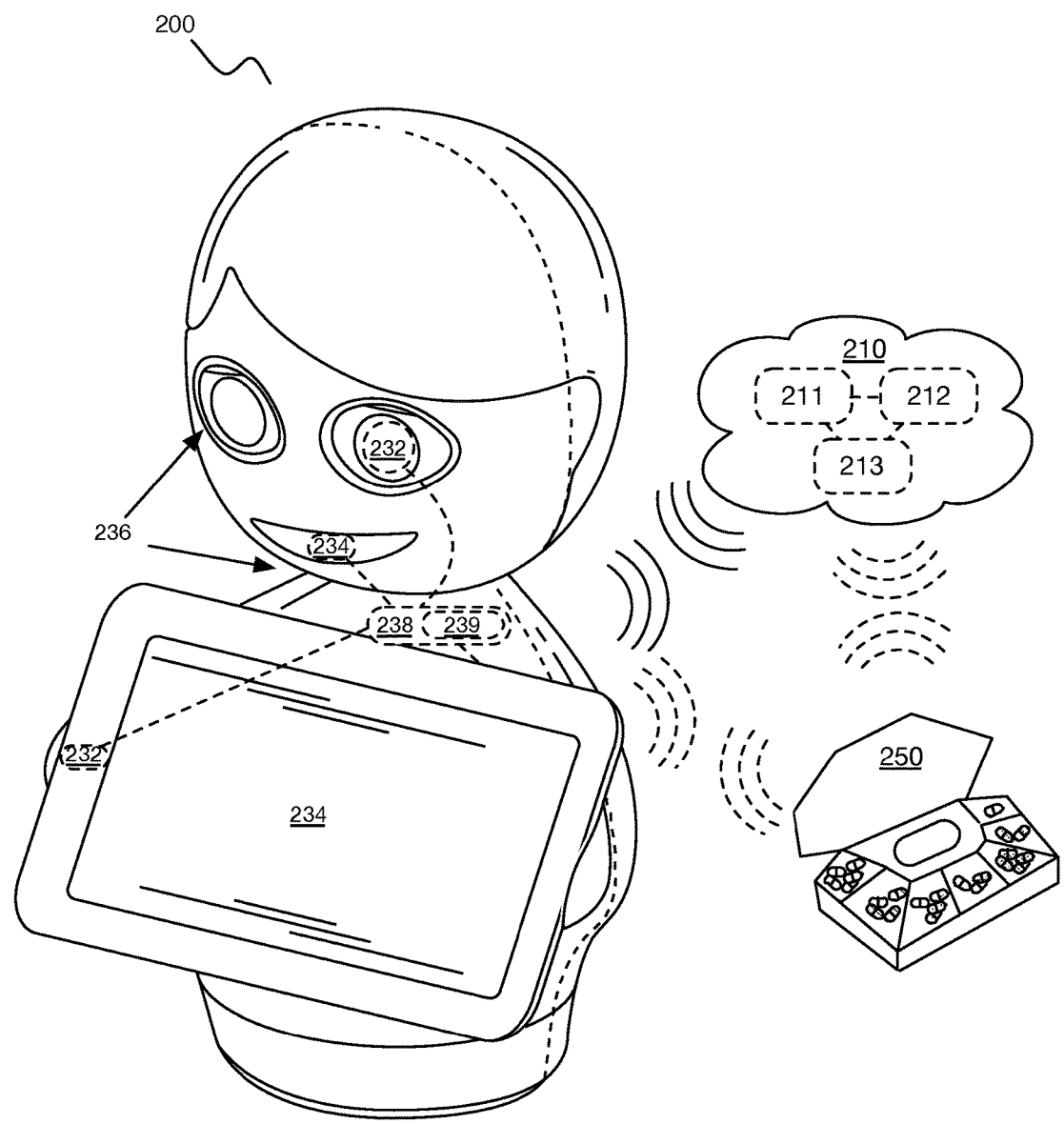
FIG. 10 depicts an example of a companion robot in an embodiment of a system.

The method 100 is preferably implemented, at least in part, by one or more embodiments, variations, or examples of the system 200 described in Section 4 below; however, the method 100 can additionally or alternatively be implemented using any other suitable system and/or system components. In a specific application, the method 100 is implemented using a robot companion, a specific example of which is shown in FIG. 10, that resides within a home environment of a patient and interacts with one or more patients on a regular basis (e.g., daily, hourly, etc., in between clinical visits, in addition to clinical visits, etc.) in order to enable close monitoring of the patient(s) in a non-intrusive, but engaging manner. The method 100 and/or system 200 can further be integrated into a platform (e.g., a cloud-based system) for collecting and sharing real-time data about the challenges each of a population of patients faces, as well as progress of each patient toward his/her respective health-related goals. The platform can additionally or alternatively improve patient care and outcomes at population-wide and individual scales, with targeted analyses of data collected from each patient.

2. Benefits.

The method 100 and system 200 can provide several benefits over conventional approaches for improving patient engagement (e.g., with medication adherence). First, the technology can effectively engage the patient by leveraging theories of relational and behavioral psychology in adapting robot communications to each patient at different points in time. Additionally or alternatively, the technology can leverage state-of-the-art medical practices for generating medically effective robot interaction plans (e.g., for communicating with a patient through conversation and animation) and/or delivering treatments to the patient in real-time.

Second, the technology can enable continuous patient management outside of (and/or within) a medical setting (e.g., a hospital), thereby facilitating decreased costs and increased efficacy of treatment. The companion robot and associated technology can interact with the patient (e.g., daily; in response to trigger conditions such as medical emergencies; etc.) in any suitable setting to help improve outcomes through education, facilitation of adherence to a medical regimen, personalized engagement tools (e.g., personalized patient-robot interaction plans for different patients), and/or other suitable venues.

Third, the technology can leverage a network of companion robots and patients (e.g., while maintaining HIPAA-compliance) to collect granular data for generating insights into patients, drawing commonalities between patient populations, and/or other suitable purposes in improving patient care management (e.g., by a care provider).

Fourth, the technology can transform a particular article to another state or thing. For example, the technology can transform one or more of: a companion robot (e.g., controlling the companion robot to communicate to a patient and to animate based on personalized interaction plans generated from a series of patient conversations with the companion robot, etc.), a supplementary device (e.g., activating a medication dispenser with the companion robot to deliver a scheduled medication to a patient, etc.), and/or any other suitable components.

Fifth, the technology can confer improvements to the functioning of computer-related technology. In a first example, the technology can amount to an inventive distribution of functionality across a network of one or more: companion robots (e.g., executing personalized interaction plans for communicating with and developing relationships with patients, based on historic conversations with patients, etc.), interaction engines (e.g., developing patient models and goals based on user inputs across users in order to use in generating personalized interaction plans), and/or any other components such as supplemental devices. In a second example, the technology can improve computational accuracy of selecting conversation components and/or animation components suited to achieving patient goals (e.g., based on analyzing efficacy of previously selected conversation components and/or animation components in achieving the goals). In a third example, the improved computational accuracy can lighten the computational processing load on one or more companion robots by enabling the companion robot(s) to output fewer communications and/or animations to achieve a given patient goal. However, the technology can provide any other suitable benefits in the context of using non-generalized systems to improve patient engagement.

3.1 Method—Receiving User Inputs.

Block S110 recites: receiving a set of user inputs from the patient at an interaction engine (e.g., computing system) associated with a companion robot. Block S100 functions to collect and/or retrieve data pertaining to features of the patient and data pertaining to interactions between the patient and the companion robot. Block S100 can include receiving the set of inputs from an input device (e.g., keyboard, keypad, mouse, touchscreen, touchpad, joystick, remote control, microphone, camera, etc.), where the inputs are provided by the patient and/or a patient-associated user (e.g., healthcare entity, guardian, relative, significant other, etc.). Block S110 can additionally or alternatively include receiving the set of inputs by way of the companion robot (e.g., through a wireless communication system of the companion robot after collecting the user inputs at sensors and/or input devices integrated with the companion robot), directly from the patient, an entity associated with the patient, and/or any other suitable entity. In one specific example, Block S100 can include receiving inputs from optical sensors (e.g., of a camera module, of a video module) of the companion robot, audio sensors (e.g., of a microphone unit) of the companion robot, and a user interface (e.g., a touch screen/touch pad for engaging the user in text-based conversations) integrated with the companion robot. In another specific example, Block S110 can additionally or alternatively include receiving inputs from capacitive touch sensors integrated into the companion robot (e.g., at a head region of the companion robot, at a shoulder region of the companion robot, at a limb region of the companion robot, at a hand region of the companion robot, etc.).

Block S110 can additionally or alternatively include receiving the set of inputs through electronic health records (EHRs) of the patient. In still other variations, Block S100 can additionally or alternatively include receiving inputs derived from a supplementary device (e.g., a wearable device) associated with the patient (e.g., directly using a wireless data link, indirectly using a wireless data link, through application programming interfaces, through health data aggregation applications of a mobile device, etc.). In a specific example, Block S100 can include querying a plurality of supplementary devices (e.g., through wireless communication, API requests tailored to different supplementary devices, etc.) with data requests for data associated with the patient. Block S110 can, however, additionally or alternatively include receiving the set of inputs from any other suitable source.

In Block S110, the set of inputs can include inputs related to the personality of the patient, inputs related to the mood/emotional state of the patient, inputs related to biographical information of the patient, inputs related to medical information of the patient, and/or any other suitable inputs. The inputs can be directly provided by the patient, and/or can additionally or alternatively be indirectly provided by any other suitable means. Furthermore, inputs of the above listed categories can overlap across categories, can inform inputs of other categories, and/or can be derived from inputs of multiple categories in any suitable manner.

Regarding Block S110, inputs related to the personality of the patient can be informative of personality traits of the patient (e.g., openness, experience, conscientiousness, extraversion, and neuroticism within a five factor model, other factors from other personality trait models, etc.) and/or can be informative of the personality types (e.g., according to a Myers Briggs categorization, etc.) of the patient. In specific examples, inputs informative of the personality of the patient can include: inputs from EHRs of the patient informative of personality traits and/or types; inputs received at a touch screen integrated with the companion robot related to conversation content between the patient and the companion robot; inputs received at audio sensors of the companion robot related to conversation content between the patient and the companion robot; inputs received at image sensors of the companion robot related to conversation content between the patient and the companion robot; inputs received at a smartphone and/or other personal device of the patient; and inputs received at sensors capable of detecting touch (e.g., capacitive sensors, force sensors, etc.) of the companion robot related to physical interactions between the patient and the companion robot. However, personality-related inputs can be defined and/or derived in any manner.

Regarding Block S110, inputs related to the mood/emotional state of the patient can be informative of a temporary mood/emotional state of the patient, and can be derived from one or more of: facial expressions of the patient captured by image sensors, speech (e.g., speech content, speech tone, etc.) captured by audio sensors, speech captured from inputs at a touch screen of the companion robot, speech captured in any other suitable manner, analysis of events of the patient (e.g., from biographical data extracted from conversations with the patient, from biographical data extracted from posts associated with the patient in electronic social networking applications, from digital communication received and/or transmitted to personal devices of the patient, etc.), and/or any other suitable source.

Regarding Block S110, inputs related to biographical information of the patient can be informative of: contextual information of the patient (e.g., name, appearance, etc.), relationship information of the patient (e.g., family information, social network information, professional network information, relationship status, etc.), demographic information of the patient (e.g., nationality, ethnicity, age, gender, etc.), interests of the patient (e.g., likes, dislikes, hobbies, etc.), life events of the patient (e.g., regular events, irregular events, etc.), locations of the patient (e.g., places relevant to the life of the patient), and any other suitable biographical information. User inputs related to biographical information can be obtained in any manner described above, and/or in any suitable manner.

Regarding Block S110, inputs related to medical information of the patient can be informative of: medication regimens of the patient, side effects of medications of the patient, interactions between medications of the patient, allergies of the patient, conditions of the patient, mental health of the patient, mobility of the patient, exercise behavior of the patient, diet of the patient, weight of the patient, medical history of the patient, other treatment regimens of the patient, preferred medical providers of the patient (e.g., hospitals, pharmacies, clinics, caretakers, etc.), medical device data (e.g., datasets collected with medical devices, historical medical device types that the patient has used, current medical device types, etc.), and/or any other suitable medical information. Similar to the method 100 aspects described above, user inputs can be extracted in any suitable manner.

Regarding Block S110, the patient can be characterized by one or more of: medical condition, demographic information (e.g., gender, age, marital status, ethnicity, nationality, socioeconomic status, sexual orientation, etc.), living situations (e.g., living alone, living with pets, living with a significant other, living with children, etc.), dietary habits (e.g., omnivorous, vegetarian, vegan, sugar consumption, acid consumption, etc.), behavioral tendencies (e.g., levels of physical activity, drug use, alcohol use, etc.), level of mobility (e.g., related to distance traveled within a given time period), and/or any other suitable trait that is relevant to health improvement. In one specific example, the patient can be of a population of patients for whom adherence (e.g., medication adherence) is an issue. In another specific example, the patient can additionally or alternatively be of a population of elderly patients. In another specific example, the patient can additionally or alternatively be of a population of cancer patients. In another specific example, the patient can additionally or alternatively be of a population of patients needing congestive heart failure (CHF) management. Patient models (e.g., in Block S120), patient goals (e.g., in Block S125), interaction plans (e.g., in Block S130) and/or other suitable components can be determined and/or executed in different manners for different populations. However, patients can additionally or alternatively have any other suitable characteristics.

Block S110 can be performed at predetermined time intervals (e.g., retrieving user input data every day in response to scheduling companion robots to transmit collected user inputs to the interaction engine on a daily basis, etc.), in response to and/or concurrently with a trigger condition (e.g., a companion robot collecting a new set of user inputs from a patient interacting with the companion robot; the companion robot receiving a threshold amount and/or types of user inputs; receiving user input data at a webhook endpoint configured to receive transmissions by a user input source; etc.), and/or at any suitable frequency or time in any suitable temporal relationship with other portions of the method 100.

In a variation, Block S110 can include scheduling data requests for user input data. In examples, each companion robot of a plurality can be associated with a communication address (e.g., unique, non-unique, etc.), where Block S110 can include: generating and transmitting a plurality of data requests addressed to different communication addresses of the plurality of companion robots. Any number of data requests can be generated, transmitted, and/or otherwise processed in serial, parallel, and/or at any time for any types of sources of user input (e.g., companion robots, EHR databases, user devices, etc.). In another variation, Block S110 can include applying computer-implemented data transmission rules for one or more companion robots. The data transmission rules preferably specify the manner (e.g., when; how, such as wireless communication; what, such as amount and/or types of user inputs and/or associated data; etc.) in which companion robots retrieve and/or transmit user input data (e.g., to an interaction engine). For example, Block S110 can apply data transmission rules specifying transmission of user input data to the interaction engine in real-time during interactions between companion robots and users; after every interaction with a patient; and/or at any suitable time. In a specific example, user inputs received in real-time can be used for performing in real-time: determination of an updated interaction plan (e.g., in Block S130); control of supplementary devices (e.g., in Block S150); initiation of telecommunication (e.g., in Block S160); and/or other suitable portions of the method 100. Block S110 can include applying different data transmission rules for different companion robots based on the individual patient (e.g., a rule specifying that the companion robot retrieve fitness wearable data for an overweight patient using a fitness wearable that is compatible with the companion robot), patient populations (e.g., a rule specifying a higher frequency of user input data transmission to the interaction engine for patients suffering from life-threatening conditions), number of patients associated with the companion robot (e.g., a rule specifying transmission of user input data in response to receiving user inputs from a threshold number of patients that use the companion robot), location of the companion robot (e.g., different data transmission rules for companion robots operating in a medical setting versus a home setting, etc.), and/or any suitable criteria. In an example, the method 100 can include: applying natural language processing algorithms to extract a sentiment from conversational user inputs collected at a microphone of the companion robot; determining that the sentiment satisfies an emergency situation trigger condition (e.g., the patient is contemplating suicide); and transmitting the user conversational inputs (and/or other associated data) in response to detecting the emergency situation trigger condition. Additionally or alternatively, applying data transmission rules can be performed in any manner, and Block S110 can be performed at any suitable time and/or frequency. However, receiving user inputs Silo can be performed in any suitable manner.

3.2 Method—Determining a Patient Model.

Block S120 recites: at the interaction engine, determining one or more patient models for the patient. Block S120 functions to determine and/or refine models that can cooperatively govern output of the companion robot for engaging the patient. As such, Block S120 and/or other portions of the method 100 (e.g., patient goals in Block S125, interaction plans in Block S130), can be used to ultimately improve outputs of the companion robot, in promoting a higher level of engagement between the companion robot and the patient.

Figure 1A:
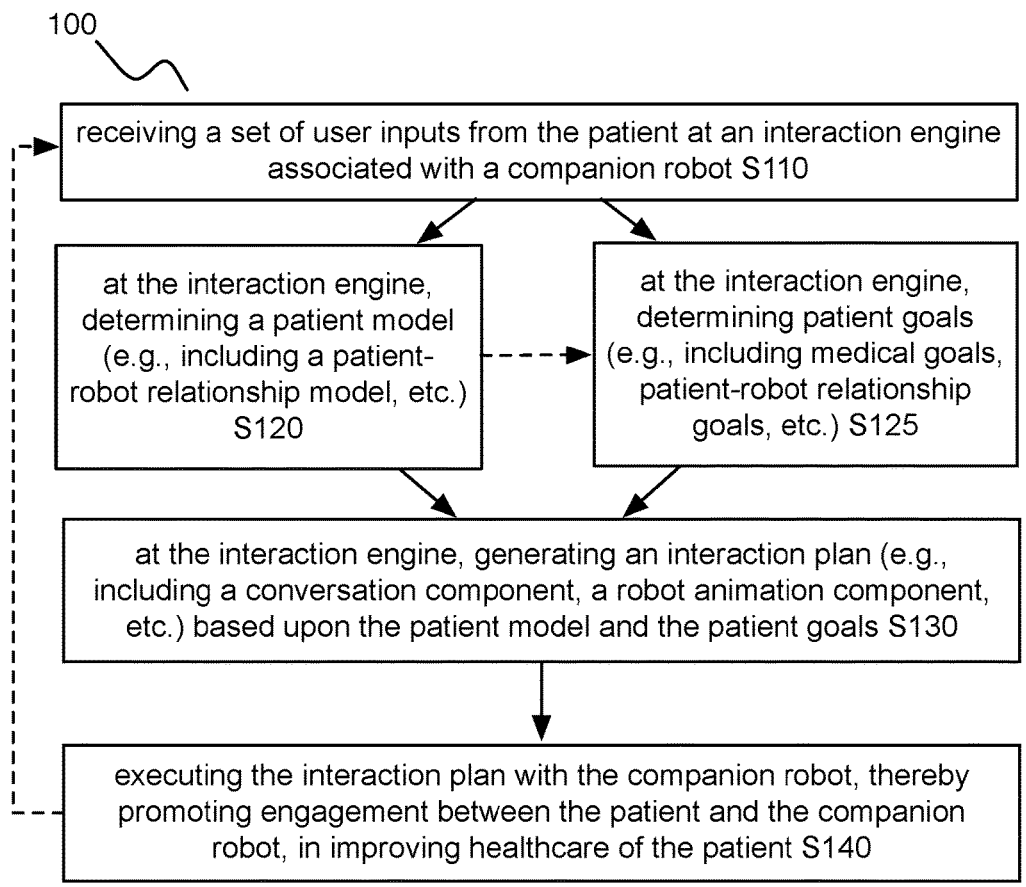
FIGS. 1A-1C are variations of an embodiment of a method for engaging a patient.
Figure 1B:
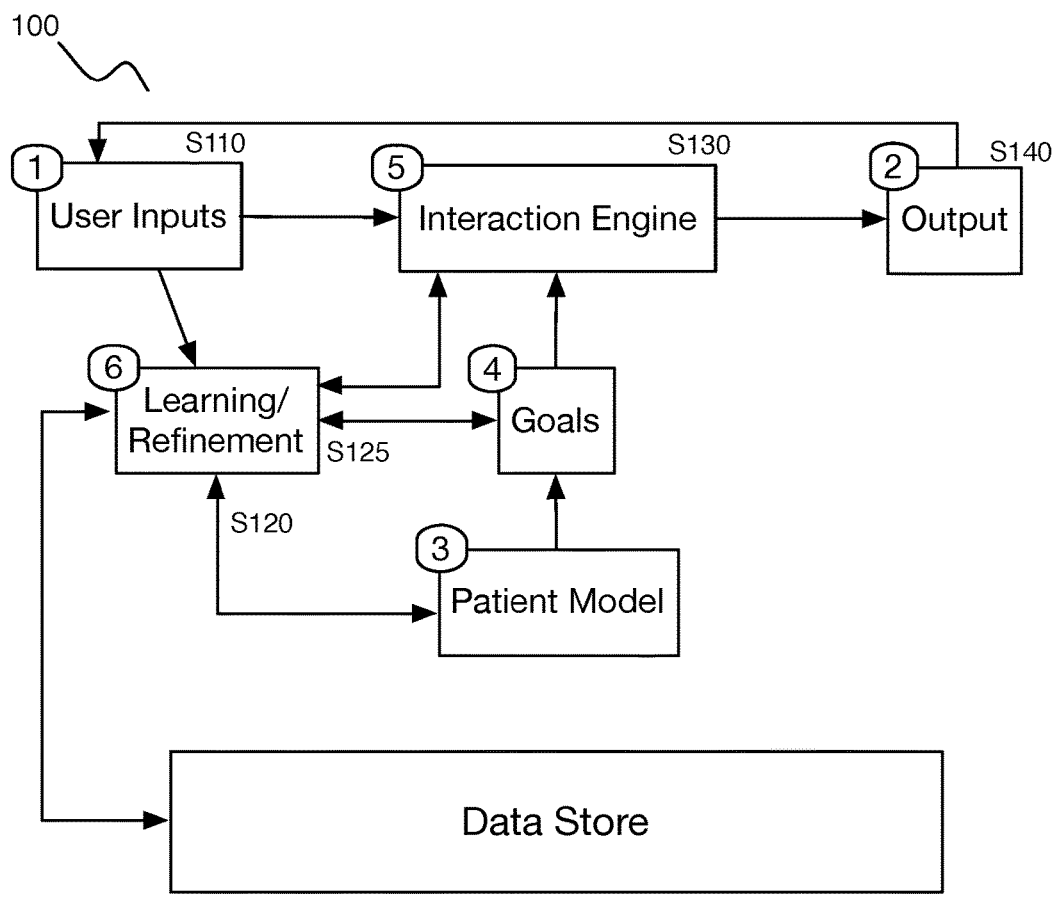
Figure 1C:
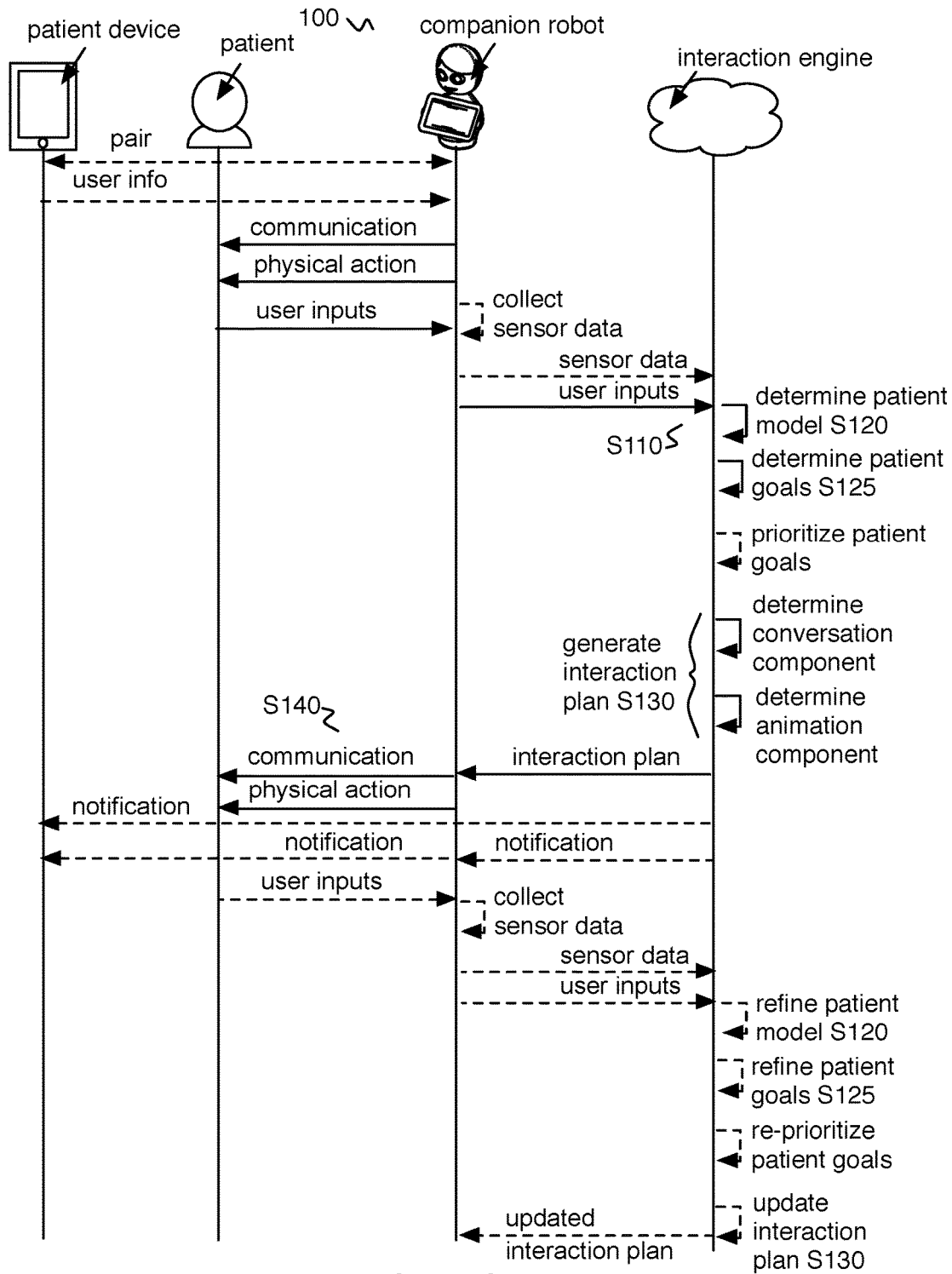
Figure 2:
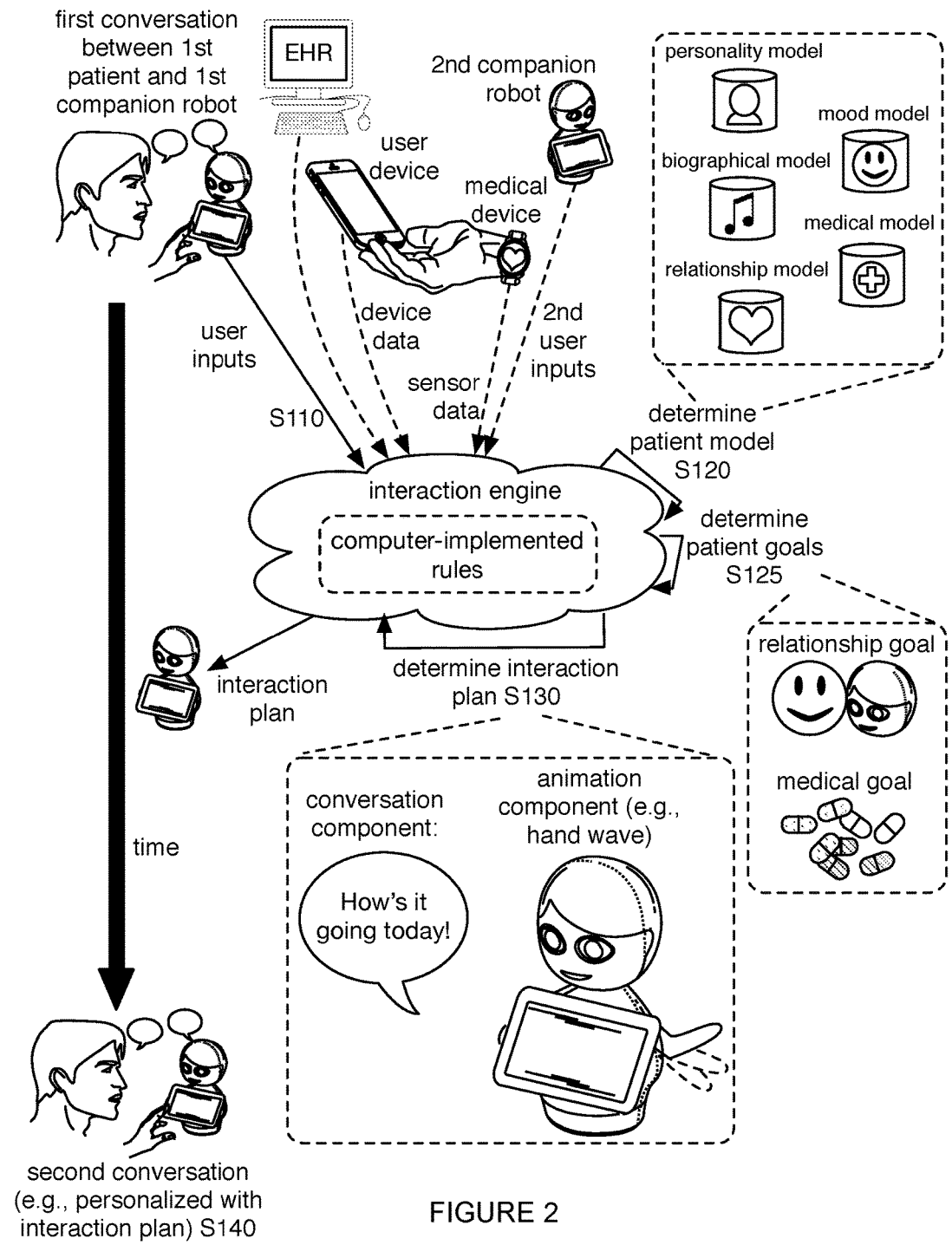
FIG. 2 depicts a schematic representation of a variation of an embodiment of a method for engaging a patient.
Figure 3:
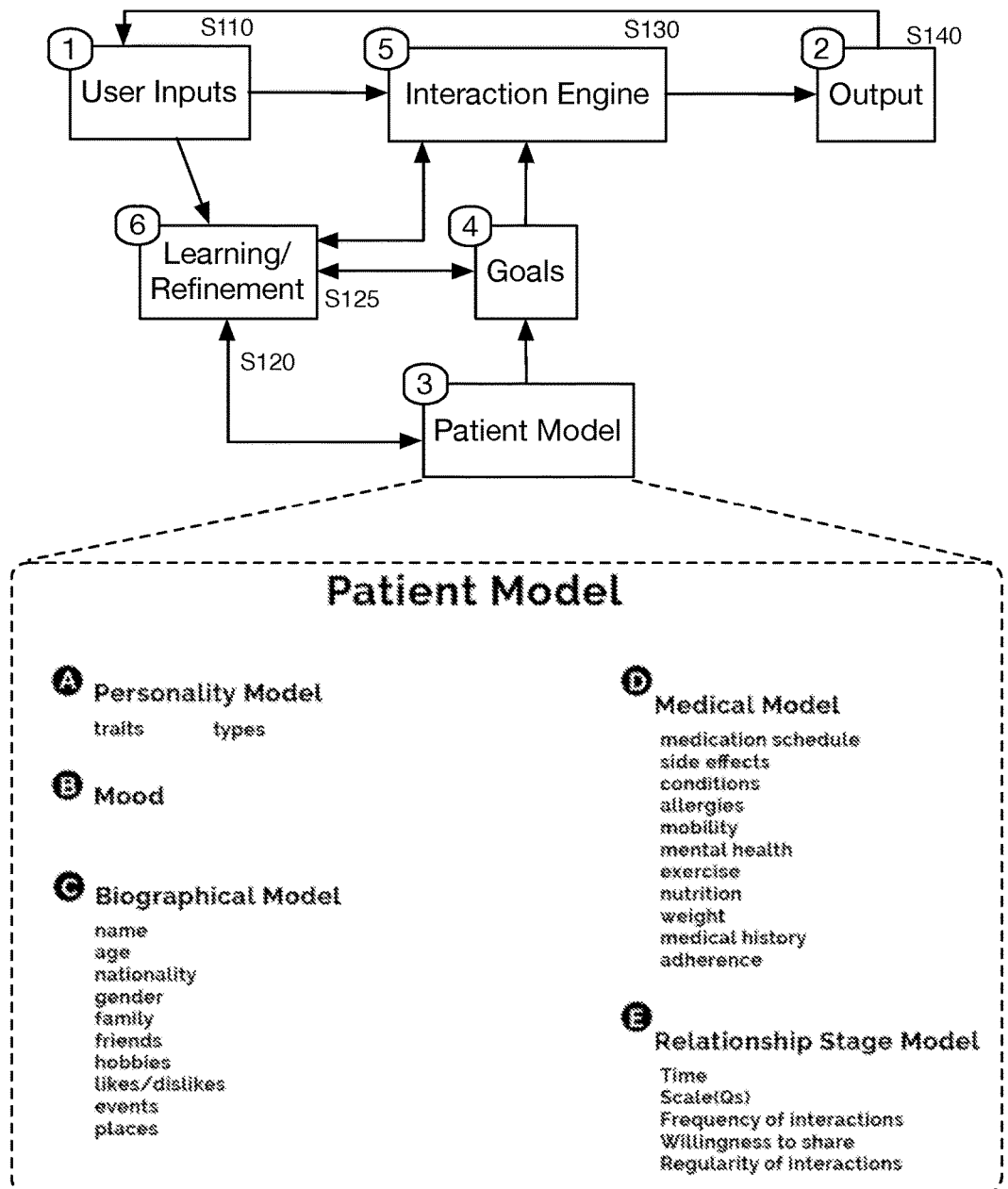
FIG. 3 depicts a variation of an embodiment of a method for engaging a patient.

In relation to Block S120, the patient model, as shown in FIG. 3, preferably includes a personality model category, a mood category, a biographical model category, a medical model category, and a relationship stage model category (e.g., a patient-robot relationship model) related to extent of engagement between the patient and the companion robot. In Block S120, refinement of the patient model preferably includes: upon receiving additional inputs in Block S110, iteratively refining hypotheses of factors of each category of the patient model. In variations, the personality model category can have factors associated with personality traits, personality types of the patient, and/or other personality-related factors; the mood category can have factors associated with transient emotional states of the patient and/or other mood-related factors; the biographical model category can have factors associated with contextual information of the patient (e.g., name, appearance, etc.), relationship information of the patient (e.g., family information, social network information, professional network information, relationship status, etc.), demographic information of the patient (e.g., nationality, ethnicity, age, gender, etc.), interests of the patient (e.g., likes, dislikes, hobbies, etc.), life events of the patient (e.g., regular events, irregular events, etc.), locations of the patient (e.g., places relevant to the life of the patient), and/or other biological factors; the medical model category can have factors associated with medication regimens of the patient, side effects of medications of the patient, interactions between medications of the patient, allergies of the patient, conditions of the patient, mental health of the patient, mobility of the patient, exercise behavior of the patient, diet of the patient, weight of the patient, medical history of the patient, other treatment regimens of the patient, preferred medical providers of the patient (e.g., hospitals, pharmacies, clinics, caretakers, etc.), medical devices (e.g., history of medical device usage, current medical devices used by the patient, data collected at the medical device, etc.) and/or any other suitable medical information; and the relationship stage model category can have factors associated with duration of time of the relationship between the companion robot and the patient, scale of the relationship between the companion robot and the patient, frequency of interactions between the companion robot and the patient, openness of communications between the companion robot and the patient, regularity of interactions between the companion robot and the patient, willingness of the patient to allow a companion robot to aid in achieving patient goals, willingness of the patient to allow a companion robot to communicate with patient-associated users (e.g., care providers, family members, other patients) about the patient, and/or other relationship-related factors.

As such, regarding Block S120, determination (e.g., refinement) of the personality model category of the patient model over time can include: processing new direct and indirect inputs associated with traits and types of the individual, and updating the current hypothesized personality model of the patient, and whether or not the patient enjoys interacting with the companion robot, based on the new inputs. In a specific example of refinement of a personality model factor, the patient can be hypothesized to have a low amount of extroversion in terms of propensity to talk to the companion robot; however, this hypothesis can be refined in Block S120 upon receiving a higher frequency of talking interactions between the patient and the companion robot in Block S110, such that the patient is now hypothesized to have a higher propensity to talk to the companion robot (which in turn, can facilitate design of interactions that promote talking between the patient and the companion robot).

Similarly with respect to Block S120, determination (e.g., refinement) of mood features of the patient model over time can include: processing new direct and indirect inputs to extract facial expressions of the patient (e.g., from video data), speech (e.g., speech content, speech tone, etc.) of the patient (e.g., from inputs provided a touch pad integrated with the companion robot, from inputs received at a microphone integrated with the companion robot, etc.), inputs associated with biographical data of the patient (described in further detail below), and any other suitable inputs. Features extracted from the inputs can include word choices selected by the patient, motions performed by the patient, amount of "small talk" that the patient is willing to engage in, average mood of the patient, personality traits of the patient, mood patterns of the patient, mood correlations of the patient (e.g., in relation to biographical events of the patient described below, etc.), mental health of the patient, and other factors associated with mood of the patient. In a specific example of refinement of a mood factor, the patient can be hypothesized to have a worse mood on Mondays, and this hypothesis can be validated and refined in Block S120 upon consistently observing through facial expressions of the patient extracted in Block S110, that the patient consistently has a pattern of poor mood on Mondays (which in turn, can facilitate design of interactions that promote cheering up of the patient on Mondays).

Similarly with respect to Block S120, determination (e.g., refinement) of the biographical model of the patient model over time can include: processing new direct and indirect inputs from which identified periodic events can be extracted, from which constant events can be extracted, from which singular events can be extracted, from which impact of interest (e.g., hobbies) on wellbeing of the patient can be extracted, from which impact of family on wellbeing of the patient can be extracted, from which impact of friends on wellbeing of the patient can be extracted, from which interaction preferences of the patient can be extracted, and from which any other suitable biographical information can be extracted. In a specific example of refinement of a biographical model factor, the patient can be hypothesized to have a higher degree of wellbeing with regular visits from all family members; however, this hypothesis can be refined in Block S120 upon observing that the patient has a lower degree of wellbeing with visits from a specific family member based on new inputs received in Block S110 (which in turn, can facilitate design of interactions that promote establishing a rapport between the patient and the companion robot in relation to venting after visits from the specific family member).

Similarly with respect to Block S120, determination (e.g., refinement) of the medical model of the patient model over time can include: processing new direct and indirect inputs associated with medication schedules of the patient, side effects of medications of the patient, conditions of the patient, allergies of the patient, mobility of the patient, mental health of the patient, exercise behavior of the patient, diet of the patient, weight of the patient, medical history of the patient, adherence of the patient, and inputs associated with one or more of the personality model, the mood, and the biographical model of the patient. In Block S120, refinement can include: identifying correlations between indirect and direct inputs of the patient (across different factors of the personality model, the mood model, the biographical model, and the medical model), predicting adherence of the patient, anticipating whether the patient will take a dose of a medication, adapting a prior schedule of interactions between the companion robot and the patient, switching between operation modes of reminding the patient vs. checking in with the patient; identifying which patient types specific interactions of the companion robot have the most impact on, observing behavior change patterns, assessing readiness for behavior change, and any other suitable refinement. In a specific example of a medical model factor, the patient can be hypothesized to have a low level of adherence to a specific medication due to side effects of the medication; this hypothesis can be validated in Block S120 upon regularly observing the side effects of the patient upon taking the medication (which in turn, can facilitate design of interactions that drive changes in the medication regimen of the patient).

Similarly with respect to Block S120, determination (e.g., refinement) of a patient-robot relationship model can be based on relationship features including any one or more: conversation features (e.g., frequency of conversations; duration of conversations, such as average duration; speed of patient response to communications by the robot; conversation content; conversation tone; patient mood over the course of conversation, such as derived from facial expression analysis; comparisons between expected conversations and actual conversations; user-initiated conversations vs. robot-initiated conversations; confusion triggers such as the frequency of the companion robot misunderstanding the patient), retention features (e.g., engagement over time; engagement trends; etc.), cross-patient features (e.g., engagement level relative other patients and other companion robots; conversation content for one patient versus another patient; other suitable comparisons of relationship features between patients; etc.); goal-related features (e.g., willingness of patient to allow companion robot to provide support for achieving patient goals; number and/or types of goals achieved in cooperation with the companion robot; etc.), supplemental features from supplemental sources (e.g., inputs from patient-associated users indicating patient's views towards the companion robot; etc.), and/or any other suitable relationship-related features. Patient-robot relationship models can be determined for patient relationships with a specific companion robot, with a specific type of companion robot (e.g., a companion robot with medication dispensing functionality vs. a conversation-only companion robot, etc.), with companion robots generally, and/or with any suitable component. Additionally or alternatively, robot relationship models can be determined for patient-associated users (e.g., patient associated user-robot relationship models), other companion robots (e.g., robot-robot relationship models, etc.), supplemental devices (e.g., supplemental device-robot relationship models, etc.), and/or any other suitable entity, where such models can be analogous to and/or different from patient-robot relationship models. However, determining the patient-robot relationship model and/or other models associated with the patient model can be performed in any suitable manner.

In a variation, Block S120 can include determining a patient model for a patient using only user inputs from the patient; using user inputs collected across patients and/or patient-associated users; and/or using any other suitable data. In another variation, Block S120 can include determining different patient model types for different patients, such as based on individual patient, patient populations, associated companion robots, and/or other suitable criteria. In an example, Block S120 can include determining and refining comprehensive mood models for patients undergoing psychological conditions (e.g., dementia, depression, etc.). In another example, for patients associated with strict privacy settings and/or permissions, Block S120 can omit determining a medical model for the patients. However, any number of types of patient models can be determined for any number of patients possessing characteristics along any suitable vector.

Regarding Block S120, as indicated above, inputs in one category of the patient model (e.g., personality model category, mood category, biographical model category, medical model category, relationship stage model category) can be derivative from other inputs in the same category and/or inputs from other categories of the patient model. Furthermore, inputs can overlap with or otherwise inform inputs of other categories of the patient model. Furthermore, an input of the patient model can be derived from combinations of other inputs, with or without weighting of specific features. Determining (e.g., generating, refining, etc.) a patient model can be performed in response to and/or concurrently with trigger conditions, such as receiving user inputs Silo (e.g., a threshold amount and/or types of user inputs; a calibration set of user inputs collected in response to an introductory conversation between the patient and a companion robot; a set of user inputs corresponding to a single conversation; etc.), but can be performed at predetermined time intervals and/or at any suitable time and/or frequency.

Additionally or alternatively, regarding Block S120, refinement of the patient model can contribute to user validation/authentication functions of the method 100, such that one or more substantially permanent features of the patient (e.g., as identified from the refinement process of Block S110) can be used to verify the identity of the patient, in cooperation with sensing functions of the companion robot. In variations, the sensing functions of the companion robot can be used to automatically verify the identity of the patient with whom the companion robot is interacting (e.g., based on motion behavior of the patient, based on facial recognition of the patient, etc.). Additionally or alternatively, the companion robot can prompt the patient to respond to verification questions based on the patient model, but using the patient model for user validation/authentication functions can be performed in any suitable manner. However, determining a patient model S120 can be performed in any suitable manner.

3.3 Method—Determining a Patient Goal.

Figure 4:
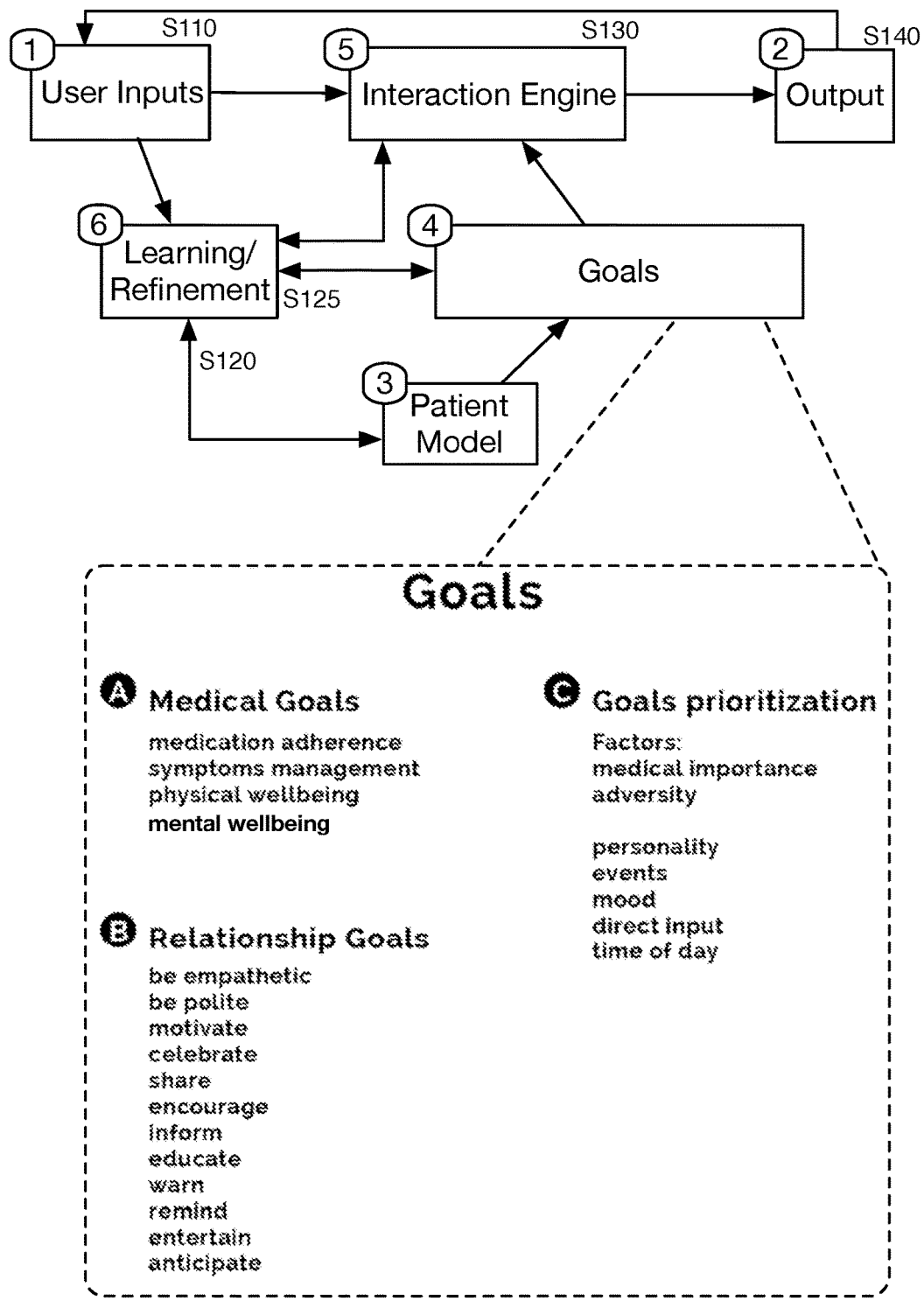
FIG. 4 depicts a variation of an embodiment of a method for engaging a patient.

Block S125 recites: at the interaction engine, determining patient goals for the patient S125, which functions to generate, refine, and/or otherwise process goals associated with the patient, which can be used in determining an interaction plan for engaging with the patient. In relation to Block S125, the aggregation of goals associated with the patient, as shown in FIG. 4, preferably includes a medical goals category associated with health-related goals of the patient, a relationship goals category associated with goals for improving or maintaining the relationship between the companion robot and the patient, and a goal prioritization category for determining the optimal priority of the various goals of the patient, but any suitable goal categories can be determined. Furthermore, refined aspects of the patient model described above can inform aspects of the goals module here, as shown in FIG. 4. As such, refinement of the goals module of Block S125 can allow the interaction engine to generate interactions that not only engage the patient, but also promote achievement of the goals of the patient in a prioritized manner.

Regarding Block S125, the medical goals category can include goals related to one or more of: medication adherence, symptom management, physical wellbeing, mental wellbeing, and/or any other suitable medical goal. The relationship goals category can include goals for content and tone of outputs of the companion robot, based on the patient model (e.g., a patient-robot relationship model), including but not limited to: goals for improving relationship features (e.g., described in Block S120), a goal for the companion robot to have desired amounts of one or more of: empathy, politeness, motivational tone, celebratory tone, sharing tone, encouraging tone, informing/educating tone, warning tone, warnings, entertaining tone, an anticipatory tone (e.g., in relation to future health-related events of the patient), nagging tone, and/or other suitable tones. Relationship goals can additionally or alternatively include one or more of: cross-patient relationship goals (e.g., relationship goals determined for a patient based on relationship goals and/or associated success parameters for other patients; relationship goals applicable to a plurality of patients; etc.), cross-robot relationship goals (e.g., relationship goals between the patient a fleet of companion robots, etc.) and/or any other suitable relationship goals for any suitable relationship and/or interaction aspects of one or more companion robots.

As such, regarding Block S125, refinement of the medical goals of the patient over time can include: processing new direct and indirect inputs informative of one or more of: adverse or negative medical events (e.g., bad side effects of a treatment or medication, worsening of a medical condition), progress in relation to a medical condition (e.g., directly determined from inputs of Block S110, predicted physical wellbeing progress based on trends in physical condition, etc. predicted mental wellbeing progress based on trends in mental health condition, etc.) adherence behavior of the patient (e.g., directly determined from inputs of Block S110, predicted adherence based on trends in adherence behavior over time, etc.), and processing of any other suitable inputs. In a specific example, the patient can be hypothesized to have a medium level of adherence to a medication regimen; however, with refinement of the adherence-related goals of the patient upon observation that the patient is improving in adherence, the adherence-related goals of the patient can be modified. Furthermore, refinement of the relationship goals of the companion robot over time can include: processing new direct and indirect inputs informative of refined personality aspects of the patient, refined biographical events of the patient, and/or refined medical information of the patient. In a specific example, the patient can be hypothesized to be moderately annoyed with interaction behavior of the companion robot (e.g., based on a refined mood model for the patient); thus, refinement of the relationship goals of the companion robot can contribute to modifications in interaction behavior that are less annoying. However, determination of relationship goals can be performed in any suitable manner.

Block S125 can be performed in response to and/or concurrently with trigger conditions, such as one or more of: receiving user inputs S110 (e.g., analogous to trigger conditions described in relation to Block S120), determining patient models (e.g., in Block S120), and/or any other suitable portion of the method 100. In examples, determining patient goals can be in response to patient model-related features satisfying predetermined conditions. In a specific example, Block S125 can be performed in response to an engagement level between patient and companion robot falling below an engagement level threshold (e.g., as determined by a refinement of the patient-robot relationship mode). However, Block S125 can be performed at any suitable time and/or frequency.

Block S125 can additionally or alternatively include prioritizing patient goals, which functions to determine a sequence for achieving different patient goals, such as through an interaction plan. Determining goal prioritization can include one or more of: generating a ranking of patient goals, refining patient goal prioritization over time, processing results of prior prioritizations of goals (e.g., rating of how well medical goals and/or relationship goals were achieved by a particular interaction plan, in order to inform future prioritizations of patient goals and/or generation of interaction plans), and/or any other suitable processes. Prioritizing patient goals can be based on one or more of: medical importance (e.g., prioritizing medical goals for at-risk patients, etc.), historical patient goal parameters (e.g., success parameters, etc.), adversity, patient models (e.g., prioritizing relationship goals for patients described as empathetic by the personality and/or mood model, etc.), events (e.g., prioritizing a relationship goal of motivating the patient in response to the patient failing to achieve a goal), user preferences (e.g., patient preferences, preferences of patient-associated users), environmental factors (e.g., time of day, weather conditions, date, temperature, etc.), and/or any other suitable criteria. In an example, Block S125 can include determining (e.g., at the interaction engine) a prioritization of a patient-robot relationship goal over a patient medical goal based on a historical goal prioritization (e.g., an efficacy of the historical goal prioritization, etc.) for the patient, where generating the interaction plan can be based on the prioritization. In a specific example, a hypothesized lack of engagement between the patient and the companion robot can contribute to a prioritization of relationship goals of the companion robot over certain other goals; however, after the patient's relationship with the companion robot is solidified, goal prioritization can be refined to increase the priority of certain medical goals. However determination of goals S125 can be otherwise performed.

3.4 Method—Generating an Interaction Plan.

Figure 5:
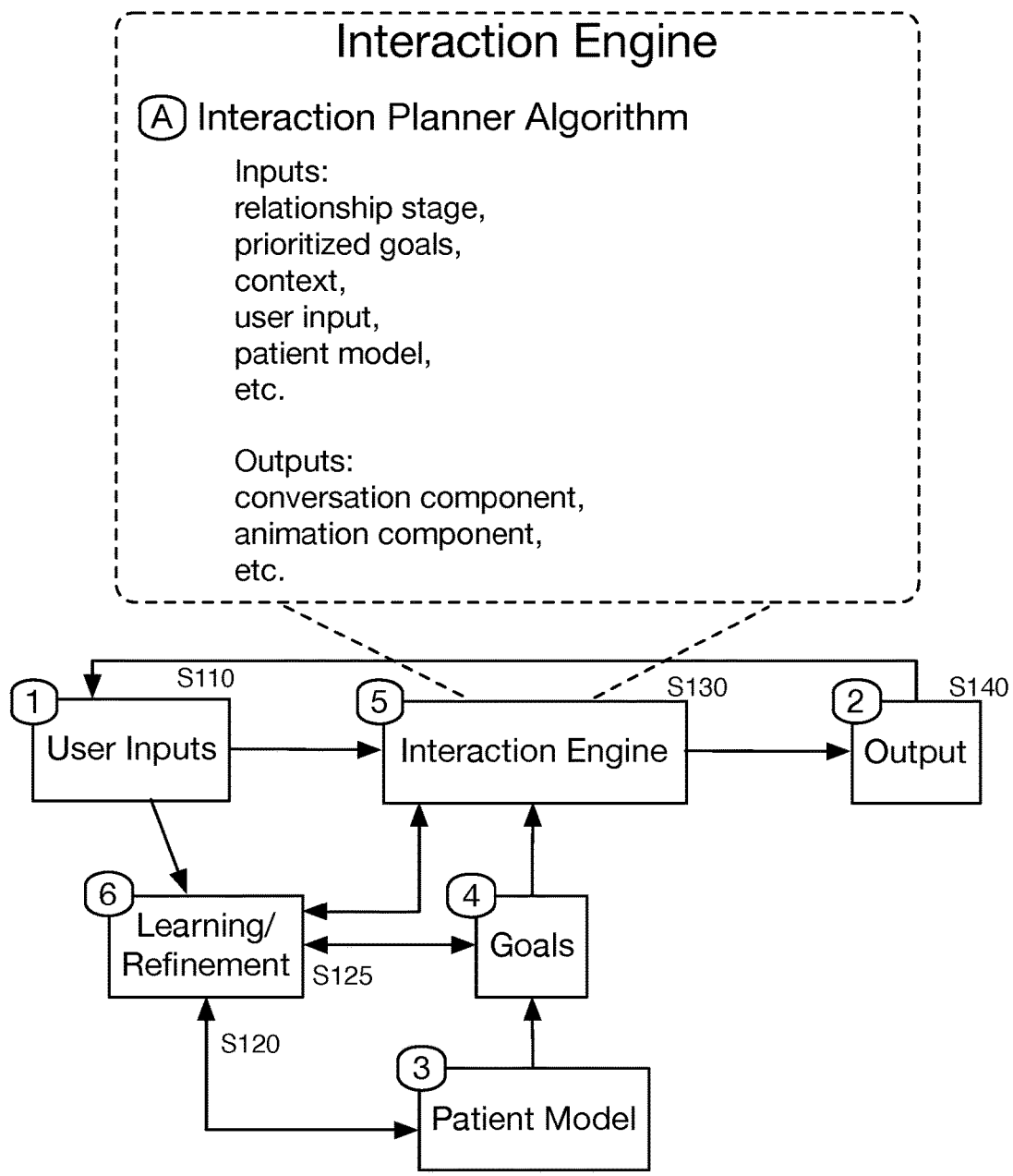
FIG. 5 depicts a variation of an embodiment of a method for engaging a patient.

Block S130 recites: determining (e.g., generating, refining, etc.) an interaction plan, including a conversation component and a robot animation component, based upon a patient model (e.g., determined in Block S110) and/or a patient goal (e.g., determined in Block S125). As shown in FIG. 5, Block S130 functions to process outputs of the most current models described above, in relation to the most current hypotheses, in designing an interaction protocol for: 1) effectively engaging the patient and/or 2) helping the patient to achieve a health goal based upon a prioritization of all health goals of the patient. Block S130 preferably includes using the goal-driven architecture refined in Block S125 to determine the most relevant and important topic(s) to engage the patient with at a certain point in time, but can alternatively be independent of patient goals. An interaction plan (e.g., interaction model) preferably specifies the manner in which one or more companion robots interact with a patient (e.g., through conversing with audio and/or visual content; physically animating actions with actuatable elements; etc.), but an interaction plan can additionally or alternatively be operable to: guide interaction with other devices (e.g., another companion robot; supplementary devices such as a user device and/or medical device), guide interaction with users associated with the patient (e.g., family members, friends, care providers, etc.), and/or facilitate any suitable interaction-related processes associated with the companion robot.

Block S130 preferably includes selecting one or more conversation components and/or animation components for the interaction plan. Conversation components preferably specify content and/or tone to be expressed by the companion robot in conversing with the patient (e.g., including guiding companion robot responses to different patient actions, etc.), but can additionally or alternatively specify one or more of: conversation scheduling (e.g., when to initiate conversation), patient goal data (e.g., patient goals to achieve with conversation components; historic success parameters for achieving patient goals for this patient and/or other patients with the conversation components; etc.), patient model data (e.g., the patient model data used in selecting the conversation component, etc.), metadata (e.g., versions; timestamps of when the conversation component was created; etc.), and/or any other suitable data. In examples, conversation components can include components (e.g., statements, questions, etc.) configured to convey personality aspects of the companion robot, configured to provide "small talk" interactions, and/or configured to help the patient improve or maintain his/her health. The conversation components can be associated with a delivery format (e.g., textual form, graphical form, audio form, touch form such as braille, etc.) for the companion robot to communicate with the patient based on the conversation component. However, conversation components can be configured in any suitable manner.

In relation to Block S130, animation components preferably specify physical actions to be performed by the companion robot (e.g., with actuatable elements of the companion robot, etc.), but can additionally or alternatively include one or more of: animation scheduling (e.g., when to perform the physical action), patient goal data (e.g., historical success parameters associated with the animation components), patient model data, metadata, and/or any other suitable data. Animation components can include one or more of: eye movement characteristics of the companion robot, eyelid movement characteristics of the companion robot, eyebrow movement characteristics of the companion robot, mouth movement characteristics of the companion robot, cheek movement characteristics of the companion robot, head movement characteristics of the companion robot, neck movement characteristics of the companion robot, torso movement characteristics of the companion robot, limb movement characteristics of the companion robot, extremity movement characteristics of the companion robot, rolling movement characteristics, walking movement characteristics, flying movement characteristics, and/or any other suitable actuatable characteristic of the companion robot with any suitable anatomical element of the robot. With the specific example of the companion robot shown in FIG. 10, animation components include eye movement characteristics of the companion robot (e.g., lateral movement, medial movement, superior direction movement, inferior direction movement, etc.), eyelid movement characteristics of the companion robot (e.g., shutting movement, opening movement, squinting movement, etc.), and neck movement characteristics of the companion robot (e.g., nodding movement, shaking movement, etc.). In variations, the companion robot can be configured to mirror and/or otherwise mimic motion/expressions of the patient (e.g., to establish a rapport between the companion robot and the patient); however, animation components can be configured in any suitable manner.

Regarding Block S130, determining an interaction plan is preferably based on one or more patient models and/or patient goals, but can additionally or alternatively be based on any one or more of: patient-associated users (e.g., patient-associated user models, goals specified by a family member, etc.), supplementary device data (e.g., medication dispenser data on adherence), other patient models and/or goals (e.g., using data associated with models and/or goals of a second patient to inform interaction plans with a first patient), and/or any other suitable data. In a variation, the method 100 can include: receiving care provider inputs associated with the health of the a patient (e.g., inputs regarding medical history of the patient; interactions between the care provider and the patient; instructions by the care provider of how to interact with the patient; trigger conditions in which to perform an action relating to the care provider, such as contacting the care provider in response to a patient conversing with the companion robot regarding emergency content; etc.), determining a care provider model (e.g., which can include any of the types of models associated with the patient model) based on the care provider inputs; and determining an interaction plan for the patient based on the care provider model (e.g., along with a corresponding patient model and/or patient goals). However, determining interaction plans based on patient-associated user data can be performed in any suitable manner.

In relation to Block S130, determining an interaction plan (and/or any other suitable portions of the method 100) can include generating and/or executing a model (e.g., an interaction plan determination model) including any one or more of: probabilistic properties, heuristic properties, deterministic properties, and/or any other suitable properties. In a first variation, Block S130 can include selecting interaction objects from a list of interaction objects to provide to the user, using the robot. In another variation, Block S130 can include generating an interaction plan based on a generating and/or applying one or more interaction trees. The interaction tree (e.g., generated with a sequence of modular sub-trees) preferably designs conversation flows with associated actions (e.g., animations, initiating teleconference calls, activating supplementary devices, etc.) that are intended to be carried out by the companion robot in relation to one or more patients. In generating the interaction tree, Block S130 can pull specific conversation components (e.g., sentences, questions, statements, phrases, etc.) from a conversation database, where each conversation component is associated with a branch of the interaction tree. Additionally or alternatively, conversation components can be generated with artificial intelligence (e.g., using artificial intelligence implementing modules configured to perform a selection process among different existing interaction trees or interaction subtrees).

Figure 6A:
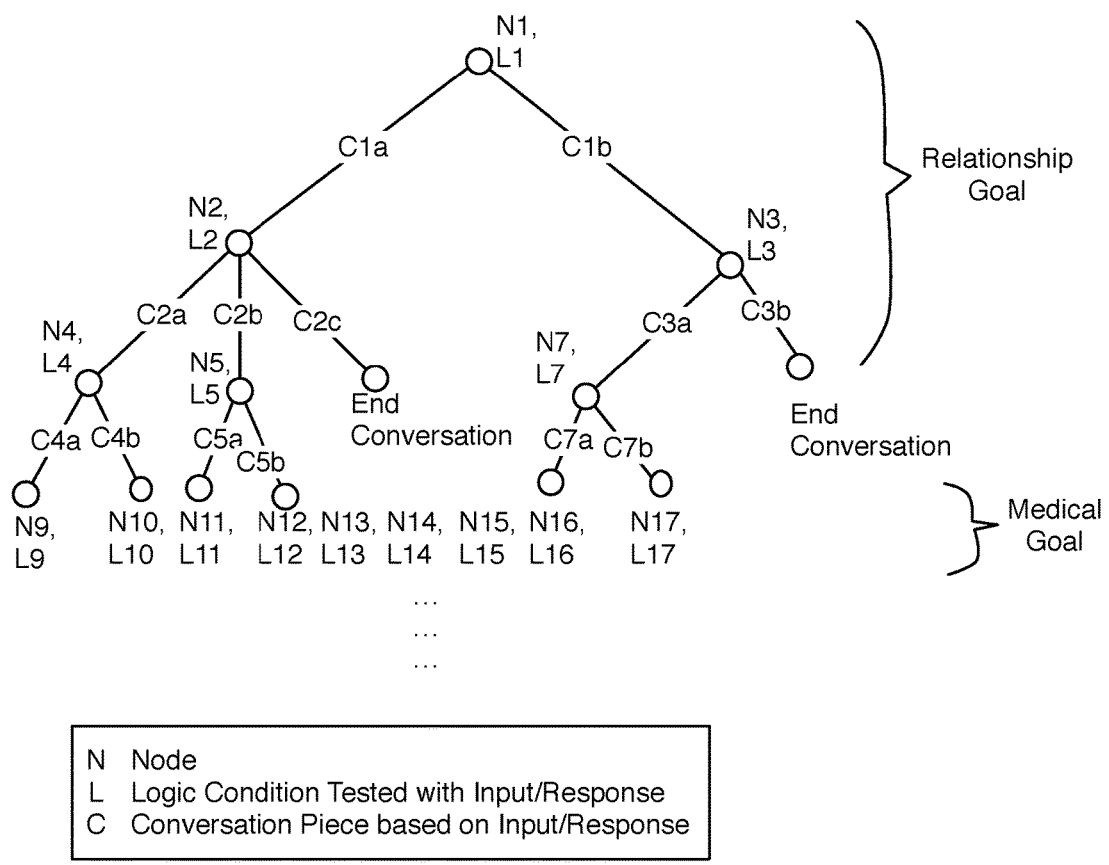
FIGS. 6A-6B depict variations and examples of components of an interaction engine in an embodiment of a method for engaging a patient.

As shown in FIG. 6A, in a variation, Block S130 can include generating a tree that includes a set of nodes and one or more branches (i.e., downstream branches, upstream branches), where each node is associated with a logic condition (e.g., different potential patient responses to content to be expressed by a companion robot when reaching a particular node), and each branch is associated with a conversation component and/or animation component configured to be executed by the companion robot. Preferably, the logic condition of a node is associated with a prioritized goal determined from the refined models of Block S120, where the conversation and/or animating component is configured to promote stronger engagement between the companion robot and the patient in the interests of achieving the goal. In one such variation, the node can have a logic condition including a decision to choose among a selection of goals to target, and each branch can contribute to associated conversation flows for achieving the prioritized goals.

Figure 6B:
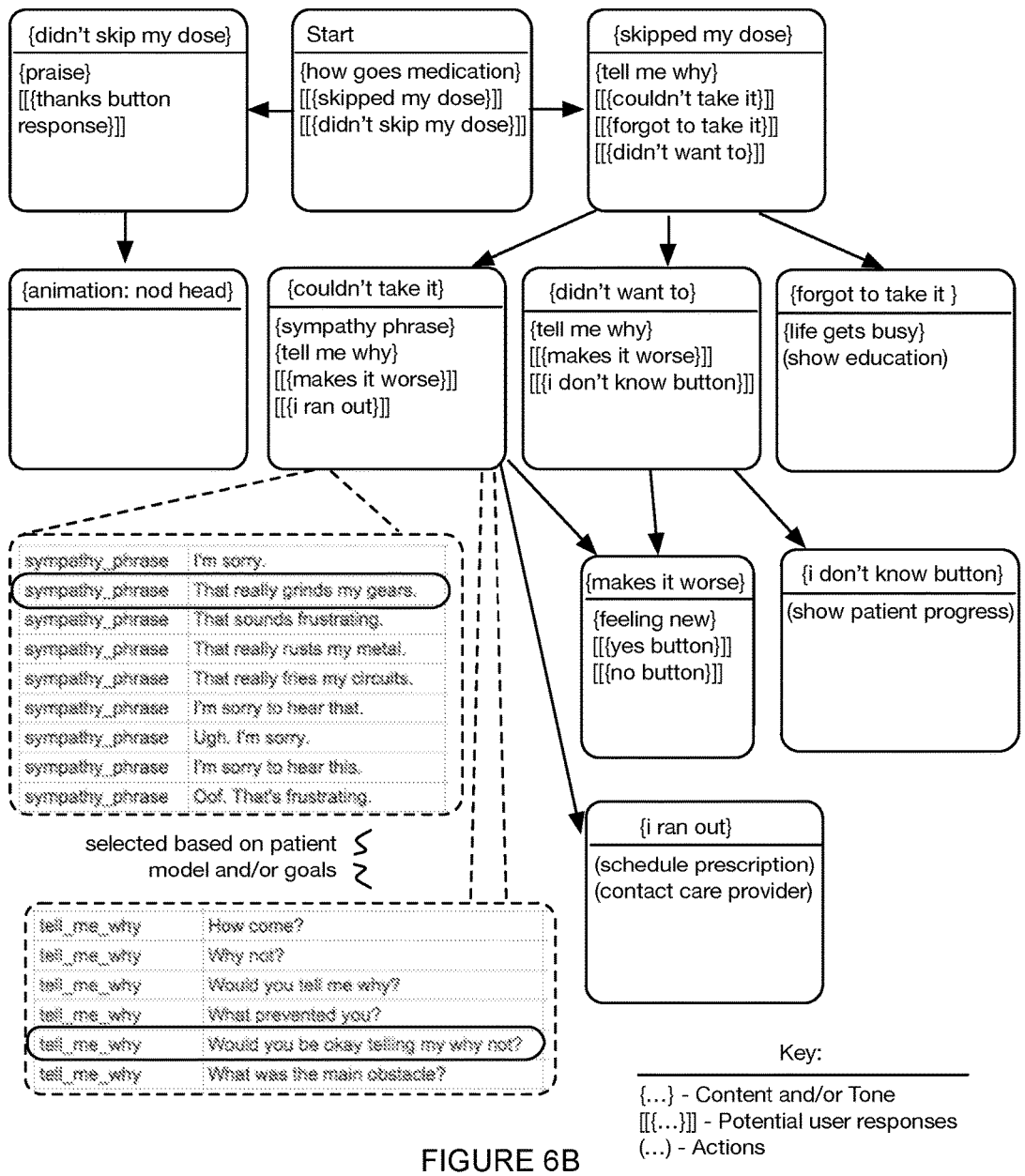

As shown in FIG. 6B, in another variation, Block S130 can include generating an interaction tree including one or more nodes associated with one or more sets of potential conversation components and one or more sets of potential animation components from which to respectively select conversation components and/or animation components for expressing content differently (e.g., different potential sentences and/or companion robot eye animations for communicating a greeting to the patient), tone (e.g., different words and/or animations used in expressing empathy to the patient), and/or other suitable interactions. The interaction tree can include branches connected to one or more nodes, where each branch can be associated with a different user response to content corresponding to the one or more nodes. Selecting one or more conversation components (e.g., from a set of conversation components available at a node) and/or animation components (e.g., from a set of animation components available at the node) is preferably based on one or more patient models (e.g., patient-robot relationship models) and/or patient goals (e.g., medical goals, relationship goals, etc.), but can be based on any suitable information. In an example, a node can dictate expression of content and a tone, where the content and the tone can be each associated with a set of potential conversation components and a set of potential animation components, and where the selection of components for content can be coordinated with (e.g., based off of; influence; etc.) selection of components for animation and vice versa.

Regarding Block S130, in a specific example, for an early relationship stage between the companion robot and the patient, a relationship-related goal configured to strengthen the relationship between the companion robot and the patient can be prioritized and, with a hypothesis that the patient responds strongly to sympathy, the node and associated branches of a interaction tree can include logic and conversation/animation components configured to show that the companion robot is sympathetic to the patient's condition. In another specific example, for a later relationship stage between the companion robot and the patient, a medical goal of the patient associated with improving adherence can be prioritized and, with a hypothesis that the patient responds strongly to education, the node and associated branches of a interaction tree can include logic and conversation/animation components configured to teach the patient why improving adherence is important to the maintenance of the patient's health. However, variations of the specific examples can be configured in any other suitable manner based on the most current refined models of Block S120.

In relation to Block S130, additionally or alternatively, the logic condition of a node of the tree generated in Block S130 can have no primary goal associated with it. For instance, the node can be a "greeting" node with branches having various conversation and animation components for greeting the patient. In another example, the node can be a "conversation closing" node with branches having various conversation and animation components for ending a conversation with a patient. However, non-goal oriented nodes can additionally or alternatively be configured in any other suitable manner.

In more detail for Block S130, in a specific example of an interaction plan having a first goal of strengthening the relationship between the companion robot and a patient who responds well to sympathy, and a second goal of promoting adherence to a medication regimen and the patient, an upstream node of a tree generated in Block S130 can have branches with conversation components that promote the patient to voice frustrations he/she is experiencing (e.g., "You seem really frustrated? Did anything happen today?"). Based on the inputs provided by the patient, downstream nodes of the tree can have branches with interaction components for appropriately responding to the frustrations inputted by the patient, where the interactions are chosen to have a sympathetic tone (e.g., "I'm really sorry to hear that ☹"). Once the sub-conversation for strengthening the relationship between the patient and the companion robot is completed, downstream nodes can be configured to promote medication adherence by the patient. One node can have logic for responding to the patient's success or failure to adhere to a medication regimen. With successful adherence, the node can have a downstream branch having interaction components associated with praise. Without failure to adhere, the node can have a downstream branch having interaction components that sympathetically ask the patient why he/she did not adhere to the regimen (as opposed to nagging interaction components). Variations of this specific example having different and/or any other suitable number of goals can, however, be generated in variations of Block S130.

In another variation, Block S130 can include processing a set of computer-implemented rules defining the interaction plan as a function of one or more variables derived from one or more of: a patient model (e.g., patient-robot relationship model), a patient goal (e.g., patient-robot relationship goal, medical goal, etc.), supplementary device data, patient-associated user data and/or any other suitable data. Computer-implemented rules can specify the types of variables to incorporate into selecting conversation components and/or animation components, weights to assign to different variables, standardization units, processing operations (e.g., data normalization, filtering, averaging, combining, etc.), and/or any other suitable aspect in relation to applying computer-implemented rules for determining an interaction plan.

In another variation, Block S130 can include generating and/or applying one or more interaction plan machine learning models. In examples, Block S130 and/or other portions of the method 100 can employ machine learning algorithm(s) that can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and/or any suitable form of machine learning algorithm. In a specific example, Block S130 can include training a neural network model (e.g., a generative neural network model without predetermined conversation and/or animation components) with an input neural layer using features derived from one or more patient models, patient goals, content and/or tone expressed by the user and/or companion robot up to the present time in a current conversation, and/or any other suitable data, where the neural network model can dynamically output conversational components, animation components, and/or any other suitable information associated with an interaction plan.

In another variation, Block S130 can include generating and/or executing different interaction plan determination models (e.g., different types of conversation trees; conversation trees versus machine learning models; etc.), where different interaction plan models can be used for different patients (e.g., different individual patients, different patient populations, etc.), different companion robots (e.g., different types of companion robots possessing different sets of sensors), and/or can be applied in different manners based on any suitable criteria. In an example, Block S130 can include generating a first set of conversation trees (e.g., including more nodes associated with empathy tones) for a first patient population (e.g., dementia patients), and generating a second set of conversation trees (e.g., including more nodes associated with achieving medical goals, such as nodes including content for asking a patient about blood glucose levels) for a second patient population (e.g., diabetic patients). In another example, a set of conversation trees can be generated for conversations regarding a first type of content (e.g., daily check-ins, etc.), and machine learning models can be used in developing interaction plans for a second type of content (e.g., potentially sensitive topics such as a patient's childhood, etc.). However, generating and/or executing different interaction plan determination models can be performed in any suitable manner.

Block S130 can include determining any number of interaction plans for any number of users (e.g., patients, patient-associated users, etc.). A given interaction plan can be used by any suitable number of companion robots, and a companion robot can executed any suitable number of interaction plans. In examples, determining an interaction plan for a first patient can be based on interaction plans for other patients (e.g., efficacy of interaction plans in achieving goals for other patients). In a specific example, the method 100 can include: generating an analysis of efficacy of a first interaction plan (e.g., to be executed by a first companion robot) for achieving a first patient medical goal associated with a first patient; generating a second interaction plan for achieving a second patient medical goal associated with a second patient, based on the analysis; and executing the second interaction plan with a second companion robot associated with the second patient. In this specific example, the method 100 can further include: receiving second user inputs collected at the second companion robot in response to executing the second interaction plan for the second patient; determining a second patient-robot relationship model based on the second user inputs and a first patient-robot relationship model (e.g., describing engagement between the first patient and the first companion robot); and updating the second interaction plan based on the second patient-robot relationship model.

In a variation, Block S130 can include generating a robot-robot interaction plan for guiding communication between two or more companion robots. Robot-robot interaction plans can specify any one or more of: communication protocols (e.g., wireless communication protocols between companion robots; protocols for communicating with supplementary devices; etc.), software update transfers (e.g., transferring a software update over-the-air to a first companion robot, and transferring the software update from the first companion robot to the second companion robot, etc.), patient data transmission (e.g., user inputs, patient models, patient goals, associated interaction plans, etc.), conversation and/or animation components for interaction between robots (e.g., a first patient's companion robot interacting with a second patient's companion robot, etc.), and/or any other suitable information. In a specific example, Block S130 can include determining a robot-robot interaction plan specifying a master/slave framework between a master companion robot and one or more slave companion robots (e.g., each operating in a same environmental setting such as a hospital); transmitting a set of interaction plans from the interaction engine to the master companion robot (e.g., through WiFi); and distributing the set of interaction plans from the master companion robot to one or more slave companion robots (e.g., through Bluetooth Low Energy).

In another variation, Block S130 can include generating a robot-supplementary device interaction plan for guiding communication between one or more companion robots and one or more supplementary devices (e.g., user device, medical device, etc.). The robot-supplementary device interaction plans can specify one or more of: communication protocols for communicating with the supplementary devices (e.g., determining control instructions for controlling the supplementary devices; specifying supplementary device addresses for transmitting communications; etc.), trigger conditions (e.g., for initiating activation of a supplementary device through a companion robot), conversation components and/or animation components (e.g., for interaction between a companion robot and a personal device of the patient), and/or any other suitable information.

In another variation, Block S130 can include generating robot-patient associated user interaction plans for guiding communication between one or more companion robots and one or more patient-associated users (e.g., family members, friends, care providers, etc.). Determining robot-patient associated user interaction plans for a user associated with a patient is preferably based on patient-associated user models (e.g., which can be determined analogously to patient models) as well as the patient models and patient goals for the corresponding patient, but can be based on any suitable information. However, determining interaction plans for robot interaction with any suitable entity can be performed in any suitable manner.

Block S130 is preferably performed in response to determining a patient model (e.g., in Block S120), and/or determining a patient goal (e.g., in Block S125), but can additionally or alternatively be performed in response to and/or concurrently with another trigger condition (e.g., analyzing efficacy of an interaction plan; determining a patient-robot engagement level below a threshold condition; etc.), performed at predetermined time intervals, and/or performed with any suitable temporal relationship to portions of the method 100. In a variation, Block S130 can include refining (e.g., updating) the interaction engine (e.g., over time) in order to, for example, improve the accuracy of the interaction engine (e.g., thereby improving the functionality of computer-related technology) in generating interaction plans with conversation components and animation components tailored to achieving patient goals. As such, refinement of the interaction engine over time can include: comparing planned conversations between the patient and the companion robot to actual conversations between the patient and the companion robot, and determining efficacy of the planned conversations in terms of medical outcomes and relationship outcomes between the companion robot and the patient. In a specific example, a planned conversation intended to promote taking of a medication by the patient can be tested, and the actual conversation can be used to refine future conversations for promoting the patient to take the medication. In another variation, Block S130 can include determining an interaction schedule specifying the timing for expressing conversation components in relation to expressing animation components, and/or timing generally for expressing conversation components and/or animation components. Additionally or alternatively, Block S130 can be performed at any suitable time at any suitable frequency.

Regarding Block S130, one or more interaction plans, associated conversation components, associated animation components, and/or other elements can be stored in an interaction database (e.g., as part of a data store of the system 200). The conversation components and/or animation components can be human crafted; however, one or more elements of the interaction database can additionally or alternatively be non-human crafted (e.g., automatically generated using artificial intelligence to craft different aspects of conversations for achieving specific goals). In a variation, generating conversation components and/or animation components with the interaction engine can involve using (initially) human-crafted conversation components and learning from responses to those conversation components using appropriate machine learning algorithms, in order to generate subsequent AI-crafted conversation components for engaging the patient. However, the interaction components can additionally or alternatively be crafted in any other suitable manner.

In relation to Block S130, each conversation and/or animation component of an interaction can be tagged (e.g., with a patient goal), such that the appropriate interaction components can be selected (e.g., for achieving patient goals) from the conversation/animation database in Block S130 for designing the interaction between the companion robot and the patient. As such, in specific examples, an interaction component (e.g., conversation component, animation component, etc.) can be tagged as one or more of: "empathetic", "sympathetic" (an example of which is shown in FIG. 6B), "polite", "motivational", "celebratory", "sharing", "encouraging", "informing", "educating", "warning", "reminding", "entertaining", "anticipatory", and/or any other suitable tone-associated tag. However, determining an interaction plan S130 can be performed in any suitable manner.

3.5 Method—Executing an Interaction Plan.

Block S140 recites: executing the interaction plan with the companion robot, thereby promoting engagement between the patient and the companion robot, in improving healthcare of the patient. Block S140 functions to enact the interaction plan through an output device (e.g., speaker, graphical display), actuatable elements, and/or other suitable components of the companion robot in order to engage the patient and elicit further interactions between the patient and the companion robot, thereby promoting building of a relationship between the companion robot and the patient. The executed interaction plan(s) are preferably determined in Block S130 and transmitted (e.g., from the interaction engine) to one or more companion robots, but interaction plans can be received by companion robots in any suitable manner. Executing the interaction plan preferably includes outputting a communication (e.g., conversational audio; updated conversational audio based on an updated interaction plan; etc.) based on one or more conversation components, and/or performing a physical action (e.g., physically performing an animation with actuating elements of the companion robot) based on one or more animation components, but can additionally or alternatively include performing any suitable action in relation to the interaction plan. Outputting a communication and/or performing a physical action is preferably coordinated and/or performed based on an interaction schedule (e.g., determined in Block S130), but can be performed at any suitable time and/or frequency, and/or in any suitable manner. Block S140 can include transmitting commands (e.g., which can be included in an interaction plan) from a control model of the interaction engine/companion robot to output elements (e.g., actuators, display modules, speakers, etc.) of the companion robot. In one variation, Block S140 can include transmitting commands that drive mechanical components of the companion robot associated with one or more of the facial and/or body motion behaviors described above. Additionally or alternatively, Block S140 can include transmitting commands that drive speaker components of the companion robot in engaging the patient with speech and/or noises. Additionally or alternatively, Block S140 can include transmitting commands that drive touch display components of the companion robot, such that the user can engage with a touch screen of the companion robot in providing responses to queries, or interacting with the companion robot using one of a set of preselected responses provided at the touch screen. However, Block S140 can be performed in any suitable manner.

3.6 Method—Extensions

Figure 8:
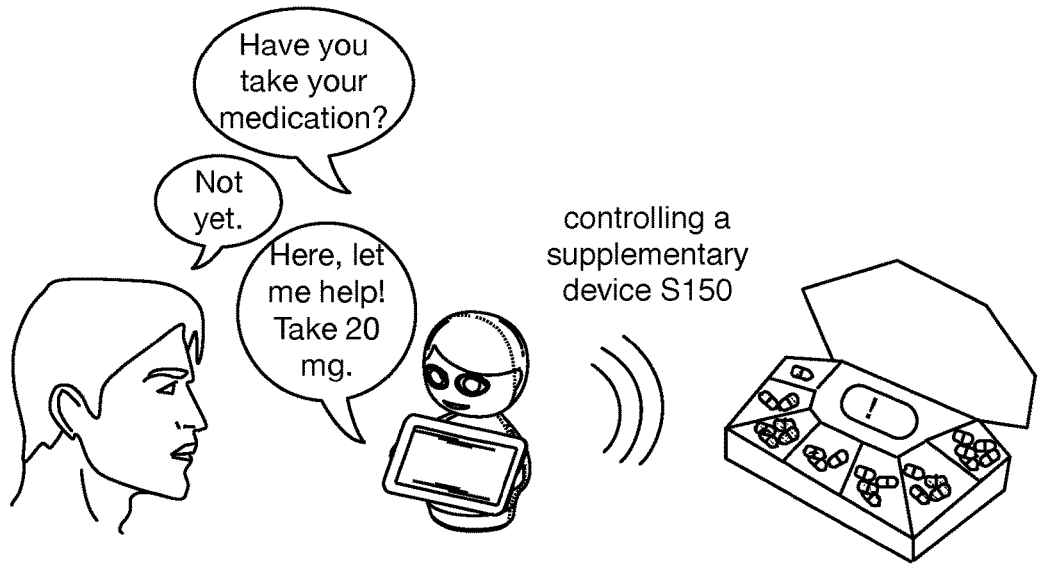
FIG. 8 depicts a schematic representation of controlling a device in a variation of an embodiment of a method for engaging a patient.

As shown in FIG. 8, the method 100 can additionally or alternatively include controlling a supplementary device with one or more companion robots S150, which functions to activate one or more supplementary devices in facilitating patient-robot engagement, patient goals, and/or in any other suitable purpose in relation to the method 100. Supplementary devices can include any one or more of: a medical device (e.g., biosignal detector, fitness wearable, cardiovascular device, head-mounted wearable device, wrist-mounted wearable computing device, etc.), a user device (e.g., smartphone, laptop, desktop computer, tablet, smart watch, toys, etc.), chatbot-enabled devices, additional companion robots, and/or any other suitable devices. Activating a supplementary device is preferably performed with one or more companion robots (e.g., through a wireless communication channel between the companion robot and the supplementary device), but can additionally or alternatively be facilitated by a device controlling engine (e.g., remote computing system; affiliated with the interaction engine; same as the interaction engine; etc.) and/or any other suitable entity. Controlling supplemental devices is preferably performed substantially concurrently with presenting communications (e.g., based on conversation components) and/or animations (e.g., based on animation components) with the companion robot, but can be performed with any suitable temporal relationship (e.g., serially, in parallel) with executing any portion of one or more interaction plans. Block S150 is preferably based on patient models and/or patient goals (e.g., medical goals), but can be additionally or alternatively be based on any suitable information. In an example, a patient-robot relationship model can be associated with user willingness for facilitation of a medical goal (e.g., medication adherence) by the companion robot, and Block S150 can include activating a supplementary device (e.g., a separate medication dispensing system; a medication dispensing system integrated into the companion robot; etc.) to facilitate the medical goal based on the user willingness and the medical goal. Block S150 can additionally or alternatively include: generating and/or transmitting a notification to a supplementary device, retrieving data from the supplementary device, determining control instructions for controlling the supplementary device, and/or any other suitable operations.

Figure 9:
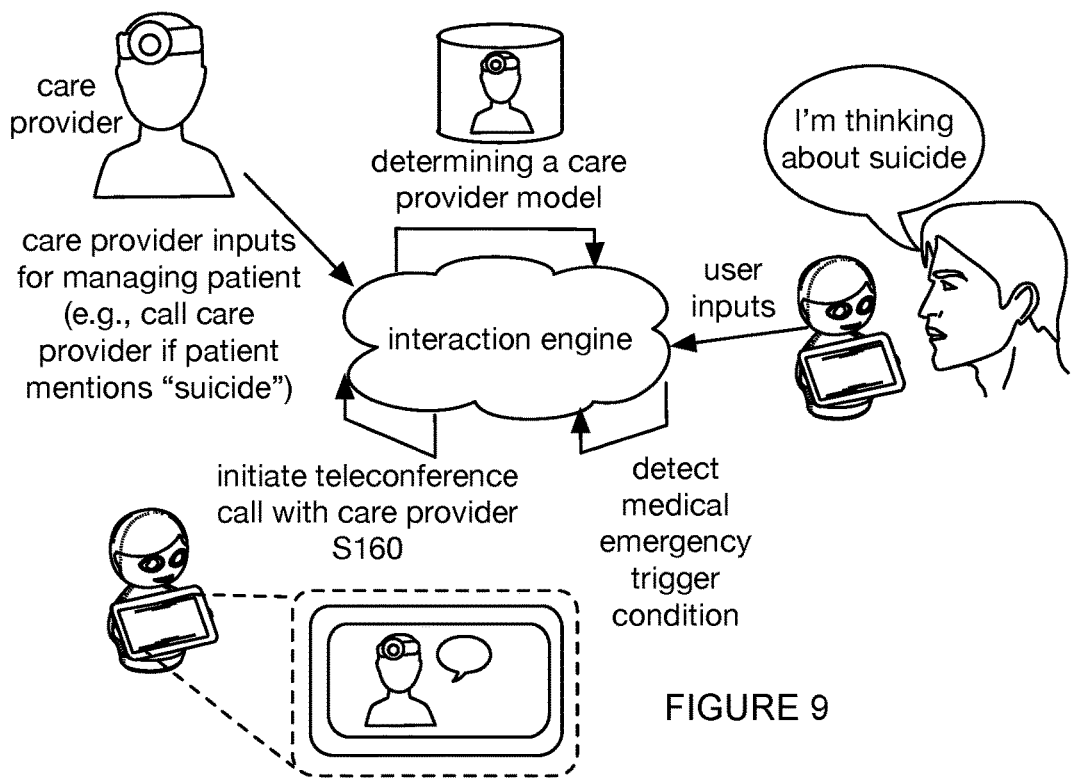
FIG. 9 depicts a schematic representation of initiating a teleconference call in a variation of an embodiment of a method for engaging a patient.

As show in FIG. 9, the method 100 can additionally or alternatively include initiating telecommunication between a patient and a user with the companion robot S160, which functions to use the companion robot to facilitate a communication channel with a user (e.g., a patient-associated user such as a care provider, another patient, etc.) to allow the patient to communicate with the user. Initiating telecommunication is preferably an action (e.g., an outcome) specified in an interaction plan (e.g., associated with a node in an interaction tree), but can be performed in relation to any suitable portion of the method 100. In an example, the method 100 can include initiating telecommunication (e.g., transmitting a video call request) substantially concurrently with expressing a conversation component (e.g., "Let me get your doctor for you") and/or an animation component (e.g., nodding) with the companion robot; however, coordinating Block S160 with executing an interaction plan can be performed in any suitable manner. However, Block S160 can be performed in any suitable manner.

The method 100 can, however, include any other suitable blocks or steps configured to increase engagement between a companion robot and a patient, and/or to achieve health-related goals of a patient. Additionally, any portions of the method 100 and/or instances of a portion of the method 100 can be performed in serial (e.g., in response to, etc.), parallel (e.g., concurrently on different threads for parallel computing to improve system processing ability for determining and/or executing interaction plans, etc.), and/or with any suitable temporal relationship.

4. System.

As shown in FIG. 10, an embodiment of a system 200 for engaging a patient includes: a companion robot 230 operable to execute an interaction plan 213 (e.g., interaction model) for communicating with the user, the companion robot including an input device 232 operable to receive user inputs from the user, an output device 234 operable to present a communication to the user based on a conversation component of the interaction plan 213, and an actuatable element 236 operable to animate an action based on an animation component of the interaction plan 213; and an interaction engine 210 (e.g., a remote computing system) operable to determine a patient model 211 (e.g., including a patient-robot relationship model, a personality model, a mood model, a biographical model, a medical model, etc.) for the patient based on the user inputs, determine a patient goal 212 (e.g., including patient-robot relationship goals, patient medical goals, etc.) for the patient based on the user inputs, and generate the interaction plan 213 based on the patient model 211 and/or the patient goal 212. The system 200 can additionally or alternatively include one or more supplementary devices 250 (e.g., described above in relation to Block S150, data stores, holographic entities, and/or any other suitable components. Any components of the system 200 are preferably configured to implement at least a portion of the method 100 described in Section 3 above; however, the system 200 can additionally or alternatively be implemented using any other suitable system.

Figure 11:
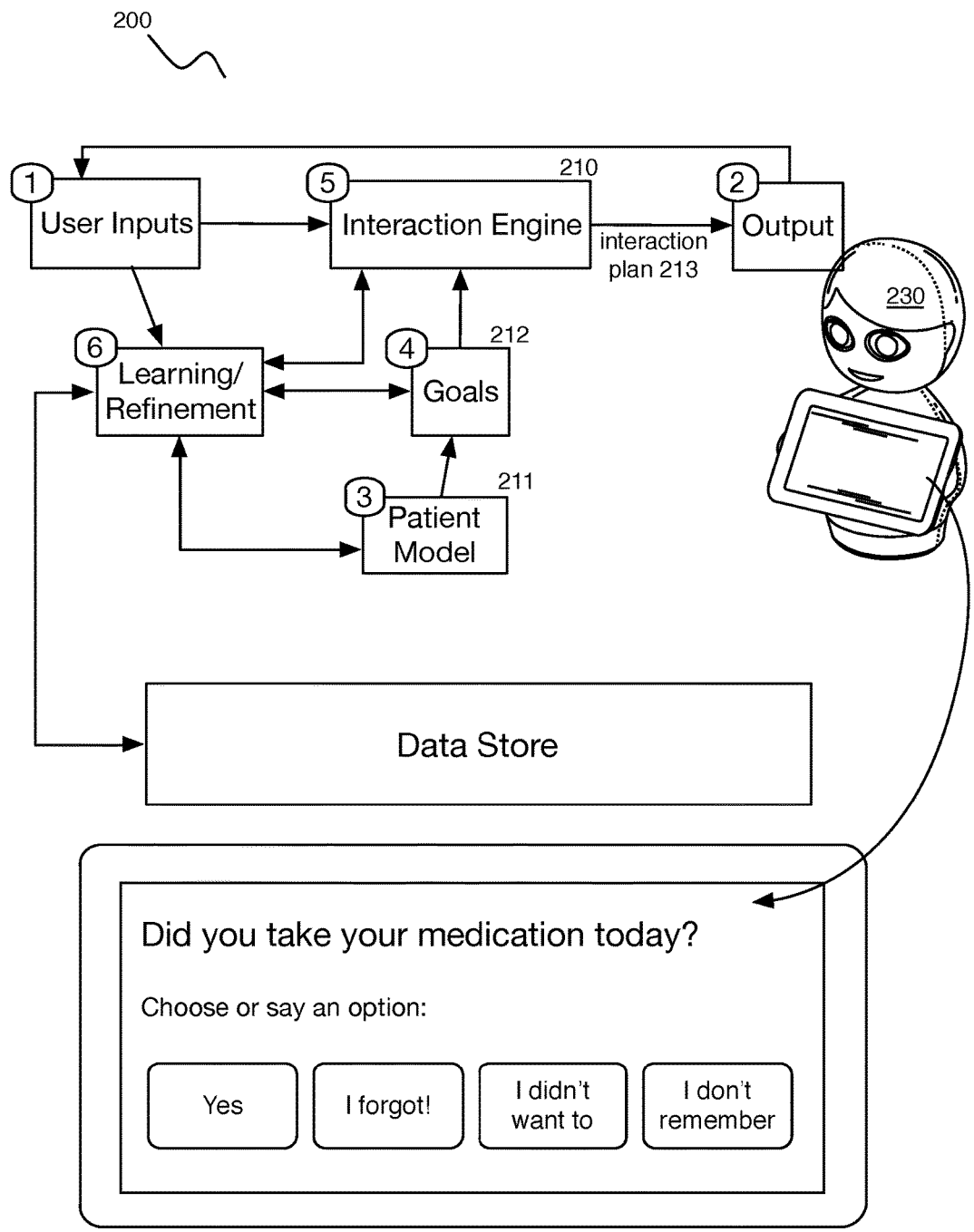
FIG. 11 depicts an example of an embodiment of a system.

As shown in FIGS. 10-11, the system 200 can include one or more interaction engines 210, which can function to process inputs related to the extent of the relationship (e.g., relationship stage) between the companion robot and the patient, prioritized goals from the goals module, contextual information of the patient, patient inputs, and/or aspects of the patient model 211, in order to output interaction plans (e.g., with conversation and animation components) operable to be implemented using one or more companion robots. As such, the interaction engine 210 preferably performs Blocks S110, S120, S125, and S130, but can additionally or alternatively perform any suitable portions of the method 100. The interaction engine 210 can be implemented in one or more of: a remote server, in the cloud, a computing system of the companion robot (e.g., a processing system 238 encapsulated within a housing of the companion robot, etc.), in a personal computing system, in a computing system of a mobile device carried by the user (e.g., a smartphone, tablet, wrist-mounted mobile computing device, head-mounted wearable computing device, etc.), where the computing executes instructions for refining models and/or executing interaction plans according to the method 100 described above. However, the method 100 can be implemented by or in cooperation with any other one or more mobile computing devices, processors, computers, computer networks, and/or other suitable components.

In a variation, the interaction engine 210 (and/or one or more companion robots 230) can generate, store, and/or retrieve user profiles for different users (e.g., patients, associated users such as family members, friends, care providers, etc.). User profiles are preferably associated with one or more patient models 211, patient goals 212, interaction plans 213, user identifiers (e.g., user account credentials, biometric credentials such as facial recognition patterns, etc.). In examples, a single companion robot can execute different interaction plans for different users, such as based on the user profiles for the different users. The companion robot can retrieve user profiles in response to recognizing users who are interacting with the companion robot, where recognition can be from any one or more of: biometric recognition (e.g., facial recognition, voice recognition, thumbprint recognition, etc.), receiving user account credentials, conversation (e.g., receiving a response to a question of "Who am I speaking to today?", etc.), and/or any other suitable form of recognition. In a specific example of a companion robot utilizing user profiles, the companion robot can be operable to collect an optical dataset of a user with an optical sensor of the companion robot; recognize the user (e.g., a patient out of a plurality of patients interacting with the companion robot) based on the optical dataset; and output a communication based on an interaction plan generated for the recognized user. In another specific example, the interaction engine 210 and/or companion robot 230 can be operable to recognize a patient-associated user (e.g., a care provider); and retrieve an interaction plan for the patient-associated user based on a corresponding user profile, where the interaction plan can include conversation and/or animation components for facilitating assistance by the patient-associated user in achieving a patient goal 212 of the patient, and where the interaction plan and/or associated components can be selected based on a user model (e.g., a relationship model specifying engagement between the patient-associated user and the companion robot; a care provider model; etc.). However, user profiles associated with different users can be configured in any suitable manner.

The system 200 can include a companion robot 230 operable to execute an interaction plan 213. The companion robot 230 functions to engage a patient using one or more conversation components and/or animation components of an interaction plan in order to, for example, achieve one or more patient goals. The companion robot can additionally or alternatively include one or more: input devices 232; output devices 234; actuatable elements 236, processing systems 238, a communication module 239 (e.g., wired; wireless; for transmitting and/or receiving data with an interaction engine 210, supplementary devices, and/or other suitable components; etc.), a housing (e.g., defining the visual appearance of the companion robot), and/or any other suitable components. The companion robot 230 preferably includes electromechanical systems (e.g., actuatable elements 236) for actuating one or more of: facial expressions and/or body movement behaviors of the companion robot, according to the method 100 above. Output devices 234 (e.g., speakers, displays, holographic displays, virtual reality devices, touch elements such as braille generators, etc.) are preferably configured to enable the companion robot to drive interactions with the patient. Input devices 232 can include any one or more of: optical sensors, touch sensors such as capacitive touch sensors, proximity sensors for sensing the position of the patient such as through radar-based sensors, location sensors such as GPS systems, motion sensors such as accelerometers and gyroscopes, audio sensors such as microphones, touch screens, keypads, keyboards, mice, joystick, and/or other suitable components that enable and/or facilitate patient interaction with the companion robot. One or more portions of the interaction engine 210 described above can be integrated with the companion robot 230; however, in alternative variations, the companion robot can serve as a conduit for interaction (e.g., through input devices 232 and output devices 234) with the patient, with computing systems implemented in components distinct from the companion robot 230.

Figure 7:
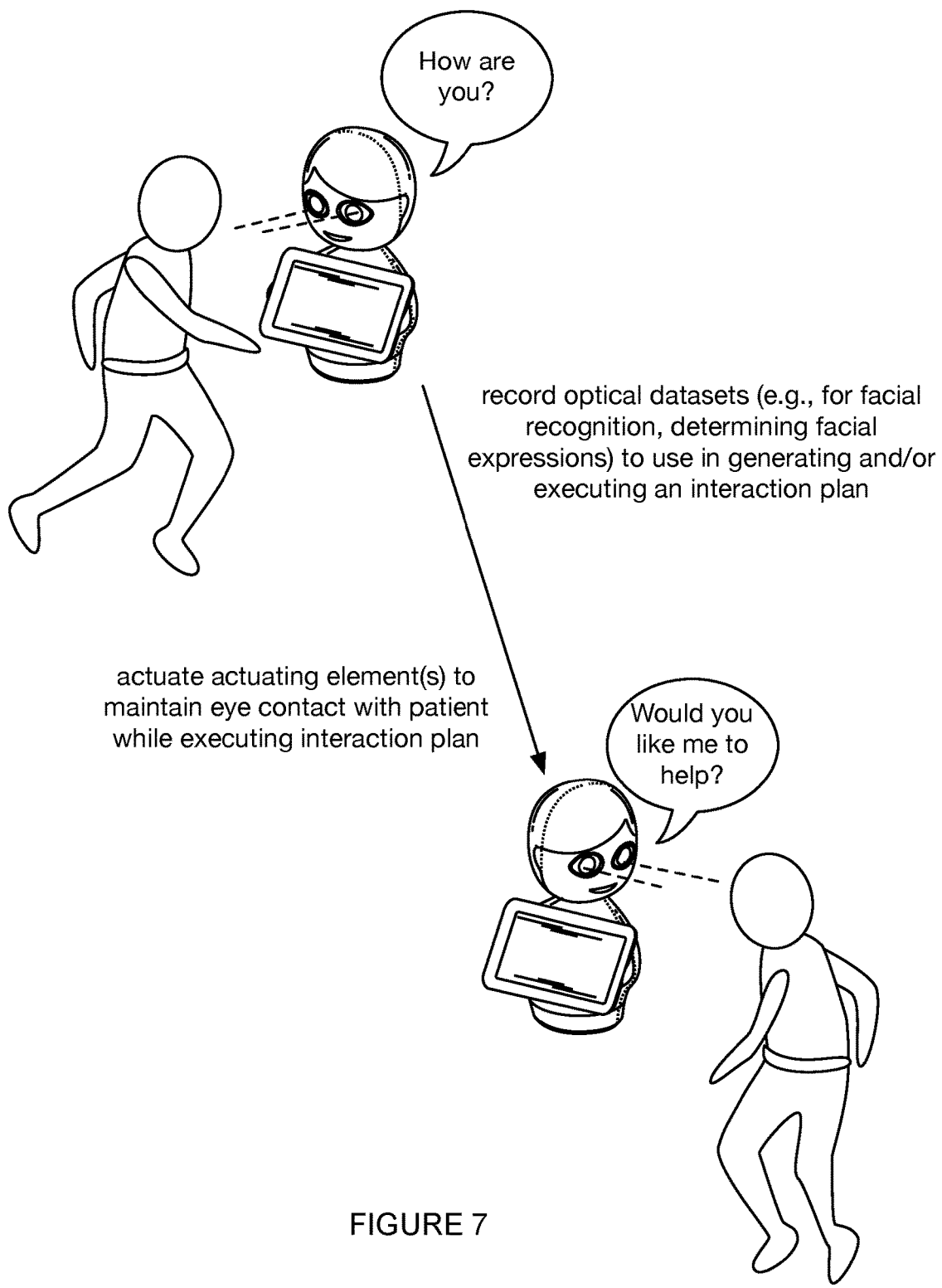
FIG. 7 depicts a schematic representation of a companion robot animation in a variation of an embodiment of a method for engaging a patient.

In a variation, the companion robot 230 can include one or more optical sensors (e.g., cameras, light sensors, etc.) operable to capture optical datasets of the patient, of patient-associated users, and/or of any suitable entity. Optical datasets can be used for: object classification (e.g., recognizing users, associated objects, environmental settings, supplementary devices, etc.), position determination (e.g., position of user), emotion recognition (e.g., based on captured facial expressions, which can be used independently and/or along with other suitable data for determining models such as user-robot relationships, etc.). In another example, the optical sensor can track a patient (e.g., keep a patient in the field of view of the optical sensor). In a specific example, the companion robot 230 (and/or other component of the system 200) can include a processing system 238 operable to determine a position of a user (e.g., patient, patient-associated user) relative the companion robot based on an optical dataset captured by the optical sensor of the companion robot, where an actuatable element 236 can be operable to animate an action (e.g., actuate the companion robot eyes toward the user to maintain eye contact with the user; actuate, along lateral and longitudinal axes, a companion robot head physically mounting the optical sensor, as shown in FIG. 7; etc.) based on position of the user (e.g., head of the user). However, optical sensors can be configured in any suitable manner.

The system 200 can include any number of companion robots 230. The network of companion robots can be interconnected (e.g., wirelessly communicating to each other through Bluetooth; through WiFi with the interaction engine 210 as an intermediary, etc.), independent of each other, connected to the interaction engine 210, and/or otherwise configured. In an example, the system 200 can include a second companion robot 230" (e.g., in addition to a first companion robot 230') operable to execute a second interaction plan 213 (e.g., second interaction model) for interacting with a second user, where the second interaction plan can include a second conversation component and a second animation component tailored to the second user based on a second user-robot relationship model and a second user medical goal. However, any number of companion robots 230 can be configured in any suitable manner.

As shown in FIG. 11, the system 200 can additionally or alternatively include a data store 260, which functions to store and/or transmit outputs and/or inputs of the method 100 for use by models (e.g., patient models, etc.) and/or other elements (e.g., interaction plans, etc.) implemented according to the method 100. The data store 260 can be implemented in hardware components (e.g., in servers, in computing systems, in the companion robot, etc.) and/or in the cloud, and can store data from a single patient and/or from a population of patients. As such, in one variation of the method 100 can implement learnings from a population of patients to drive and refine models for interacting with a specific patient. As such, variations of the refinement process of Block S120 and/or Block S125 above can include processing of inputs from a population of individuals, whose data is stored in and transmitted from the data store 260 described above. However, a data store 260 can be configured in any suitable manner. The system 200 can additionally or alternatively include one or more holographic entities, which function to enable non-physical interactions with a patient and/or an animated entity that the patient can interact with using a display. Additionally or alternatively, holographic entities can be configured in any suitable manner (e.g., where the companion robot is a holographic entity). However, the system 200 can be configured in any suitable manner.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. The embodiments include every combination and permutation of the various system components and the various method processes, including any variations, examples, and specific examples.

The method 100 and/or system 200 of the preferred embodiment can be embodied and/or implemented at least in part as a machine configured to receive a computer-readable medium storing computer-readable instructions. The instructions are preferably executed by computer-executable components preferably integrated with the application, applet, host, server, network, website, communication service, communication interface, hardware/firmware/software elements of a user computer or mobile device, wristband, smartphone, or any suitable combination thereof. Other systems and methods of the preferred embodiment can be embodied and/or implemented at least in part as a machine configured to receive a computer-readable medium storing computer-readable instructions. The instructions are preferably executed by computer-executable components preferably integrated by computer-executable components preferably integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but any suitable dedicated hardware device can (alternatively or additionally) execute the instructions.

As a person skilled in the art will recognize from the previous detailed description and from the figures and claims, modifications and changes can be made to the preferred embodiments of the invention without departing from the scope of this invention as defined in the following claims.

We claim:

1. A system for engaging a first user, comprising:
a first companion robot operable to execute a first interaction model for communicating with the first user, wherein the first interaction model comprises a first conversation component associated with a first animation component, the first companion robot comprising:
an input device operable to receive user inputs from the first user;
an output device operable to present a communication to the first user based on a first conversation component of the first interaction model, wherein the first conversation component comprises at least one of a question and a statement presented at the output device; and
an actuatable element operable to animate an action based on an animation component of the first interaction model, wherein the animation component comprises actuating the actuatable element, and wherein the animation component is performed concurrently with the first conversation component;
an optical sensor operable to capture an optical dataset of the first user during the output of the communication by the output device;
a processing system operable to determine a position of the first user relative the first companion robot based on the optical dataset, wherein the actuatable element is further operable to animate the action based on the position of the first user; and
an interaction engine operable to:
determine a first user-robot relationship model associated with engagement between the first user and the first companion robot, based on the user inputs and a user facial expression derived from the optical dataset;
determine a first user medical goal associated with the first user, based on the user inputs;
generate the first interaction model comprising the first conversation component and the animation component based on the first user-robot relationship model and the first user medical goal, wherein the first interaction model is generated using an interaction list comprising:
an object associated with a first set of conversation components and a first set of animation components for expressing content differently; and
a set of subobjects related connected to the object, each branch associated with a different user response to the content;
select the first conversation component from the first set of conversation components and the first animation component from the first set of animation components based on the first user-robot relationship model;
select a second set of conversation components and a second set of animation components for expressing a conversation tone differently, wherein the output device of the first companion robot is further operable to present a second communication in coordination with the first communication based on a second conversation component comprising at least one of a question and a statement, the second conversation component selected from the second set of conversation components, and wherein the actuatable element is operable to perform a second action in coordination with the first action based on a second animation component selected from the second set of animation components;
generate an analysis of the efficacy of the first interaction model for achieving the first user medical goal; and
generate, at the interaction engine, a second interaction model for achieving a second user medical goal associated with a second user, based on the analysis.

2. The system of claim 1, further comprising a second companion robot operable to execute a second interaction model for interacting with a second user, the second interaction model comprising a second conversation component and a second animation component tailored to the second user based on a second user-robot relationship model and a second user medical goal.

3. The system of claim 1, further comprising a device controlling engine operable to activate a medical device substantially concurrently with presentation of the communication by the output device and animation of the action by the actuatable element, based on the first user medical goal.

4. The system of claim 3, wherein the first user-robot relationship model is associated with user willingness for facilitation of medication adherence by the first companion robot, wherein the medical device is a medication dispensing system, and wherein the device controlling engine is operable to activate the medication dispensing system based on the user willingness and the first user medical goal.

5. The system of claim 1, wherein the interaction engine is a processing system of the first companion robot.

6. The method of claim 1, wherein the second interaction model is executed by a second companion robot, wherein the second companion robot is remote from the first companion robot.

7. A method for engaging a first patient, comprising:
at a remote interaction engine:
 receiving first user inputs collected at a first companion robot in response to outputting conversational audio for the first patient at a speaker of the first companion robot;
 refining a first patient-robot relationship model based on the first user inputs;
 refining a first patient medical goal based on the first user inputs;
 generating a first interaction plan comprising a conversation component, the conversation component comprising at least one of a question and a statement based on the first patient-robot relationship model and the first patient medical goal, wherein the first interaction plan is generated using an interaction list comprising:
  an object associated with a first set of conversation components and a first set of animation components for expressing content differently; and
  a set of subobjects related connected to the object, each branch associated with a different user response to the content;
 selecting the first conversation component from the first set of conversation components and the first animation component from the first set of animation components based on the first user-robot relationship model;
 selecting a second set of conversation components and a second set of animation components for expressing a conversation tone differently, wherein the output device of the first companion robot is further operable to present a second communication in coordination with the first communication based on a second conversation component comprising at least one of a question and a statement, the second conversation component selected from the second set of conversation components, and wherein the actuatable element is operable to perform a second action in coordination with the first action based on a second animation component selected from the second set of animation components;
 transmitting the first interaction plan from the remote interaction engine to the first companion robot;
 outputting, at the speaker of the first companion robot, updated conversational audio based on the conversation component of the first interaction plan;
 generating an analysis of the efficacy of the first interaction plan for achieving the first patient medical goal;
 generating, at the remote interaction engine, a second interaction plan for achieving a second patient medical goal associated with a second patient, based on the analysis; and
 executing the second interaction plan with a second companion robot, wherein the second companion robot is identical to the first companion robot, associated with the second patient.

8. The method of claim 7, wherein the first patient-robot relationship model is associated with engagement between the first patient and the first companion robot, the method further comprising:
 in response to the engagement satisfying a trigger condition, determining a patient-robot relationship goal at the remote interaction engine,
 wherein generating the first interaction plan is further based on the patient-robot relationship goal.

9. The method of claim 8,
wherein generating the first interaction plan comprises:
 obtaining a set of computer-implemented rules defining selection of an animation component as a function of the first patient-robot relationship model and the patient-robot relationship goal; and
 selecting the animation component from a set of animation components based on the set of computer-implemented rules, and
wherein the method further comprises animating a facial expression at the first companion robot based on the animation component.

10. The method of claim 8, further comprising determining, at the remote interaction engine, a prioritization of the patient-robot relationship goal over the first patient medical goal based on a historical goal prioritization for the first patient, wherein the generating the first interaction plan is further based on the prioritization.

11. The method of claim 7, further comprising:
 receiving, at the remote interaction engine, second user inputs collected at the second companion robot in response to executing the second interaction plan for the second patient;
 determining a second patient-robot relationship model based on the second user inputs and the first patient-robot relationship model; and
 updating the second interaction plan based on the second patient-robot relationship model.

12. The method of claim 7, wherein the second companion robot is remote from the first companion robot.

13. A method for engaging a first user, comprising:
 receiving user inputs collected at a companion robot in response to a first communication outputted for the first user by the companion robot;
 determining a first user-robot relationship model based on the user inputs;
 determining a patient model comprising a personality model associated with personality traits of the first user, a mood model associated with emotional states of the first user, a biographical model associated with contextual information of the first user, a medical model associated with a medication regimen of the first user, and the first user-robot relationship model;

determining a medical goal and a user-robot relationship goal, based on the user inputs;

generating an interaction plan comprising a conversation component selected from a first set of conversation components and associated with health of the first user, the conversation component comprising at least one of a question and a statement, based on the patient model, the medical goal, and the user-robot relationship goal, wherein the interaction plan is generated using an interaction list comprising:
- an object associated with a first set of conversation components for expressing content differently; and
- a set of subobjects related connected to the object, each branch associated with a different user response to the content;

selecting a second set of conversation components for expressing a conversation tone differently, wherein the output device of the first companion robot is further operable to present a second communication in coordination with the first communication based on a second conversation component comprising at least one of a question and a statement, the second conversation component selected from the second set of conversation components;

facilitating output of an updated communication by the companion robot based on the conversation component of the interaction plan;

generating an analysis of the efficacy of the first interaction plan for achieving at least one of the medical goal and the user-robot relationship goal; and generating, at the remote interaction engine, a second interaction plan for achieving at least one of a second medical goal and second user-robot relationship goal associated with a second user, based on the analysis.

14. The method of claim 13, wherein the second interaction plan comprises a second conversation component for communicating with a second user, the method further comprising:
- collecting an optical dataset of the second user with an optical sensor of the companion robot; and
- in response to recognizing the second user in the optical dataset, facilitating output of a second communication by the companion robot based on the second conversation component.

15. The method of claim 14, wherein generating the second interaction plan comprises selecting the second conversation component to facilitate assistance by the second user in achieving a medical goal of the first user, based on a second user-robot relationship model associated with the second user.

16. The method of claim 13, further comprising:
- receiving care provider inputs associated with the health of the first user; and
- determining a care provider model based on the care provider inputs,
- wherein generating the interaction plan is further based on the care provider model.

17. The method of claim 1, wherein the interaction engine further comprises:
- an interaction tree comprising a plurality of interaction nodes, each interaction node comprising:
  - a predetermined set of conversation components; and
  - a predetermined set of animation components; and
- a logic condition for the first user, the logic condition operable to select a conversation component and an animation component for an interaction node of the interaction tree based on a first user medical goal, wherein the selected conversation component and the selected animation component cooperatively form the first interaction model for communicating with the first user.

18. The method of claim 17, wherein the logic condition comprises a first patient model for the first user, wherein the first patient model is generated based on the first user medical goal.

19. The method of claim 18, wherein the interaction engine further comprises: a second patient model for the second user, generated based on the first patient model and the second user medical goal, the second patient model operable to select a second conversation component and a second animation component for the interaction node of the interaction tree, wherein the second conversation component and the second animation component cooperatively form the second interaction plan.

20. The method of claim 13, wherein the second interaction plan is executed by a second companion robot, wherein the second companion robot is remote from the first companion robot.

* * * * *

UNITED STATES PATENT AND TRADEMARK OFFICE
CERTIFICATE OF CORRECTION

PATENT NO. : 10,452,816 B2  
APPLICATION NO. : 15/428024  
DATED : October 22, 2019  
INVENTOR(S) : Cory Kidd et al.

Page 1 of 1

It is certified that error appears in the above-identified patent and that said Letters Patent is hereby corrected as shown below:

In the Claims

Column 27, Line 22, delete "method" and insert --system-- therefor  
Column 30, Line 14, delete "method" and insert --system-- therefor  
Column 30, Line 27, delete "method" and insert --system-- therefor  
Column 30, Line 31, delete "method" and insert --system-- therefor  
Column 30, Line 32, after "comprises:", insert --¶--  
Column 30, Line 37, after "tree,", insert --¶--

Signed and Sealed this  
Twenty-fifth Day of February, 2020

Andrei Iancu  
*Director of the United States Patent and Trademark Office*